(12) United States Patent  
Polidoro et al.

(10) Patent No.: US 6,629,956 B1
(45) Date of Patent: Oct. 7, 2003

(54) PARENTERAL FLUID TRANSFER APPARATUS

(76) Inventors: John M. Polidoro, 232 Woodmont Dr., Coventry, CT (US) 06238; Richard G. Holdaway, 25 Westgate La., Storrs, CT (US) 06268; Chad C. Smutney, 44-38 Tolland Ave., Stafford Springs, CT (US) 06076; Carl R. Sahi, 389 High St., Coventry, CT (US) 06238; Richard S. Kearns, 2618 4th Ave. West, Seattle, WA (US) 98119; Kevin J. Seifert, 714 Orchard Rd., Kinnelon, NJ (US) 07405; Gregory F. Biancardi, 95 Horizon Cir, South Windsor, CT (US) 06074; John M. Seifert, 31 Nuthatch Hill, Trumbull, CT (US) 06611

( * ) Notice: Subject to any disclaimer, the term of this patent is extended or adjusted under 35 U.S.C. 154(b) by 0 days.

(21) Appl. No.: 09/404,096

(22) Filed: Sep. 23, 1999

Related U.S. Application Data

(63) Continuation-in-part of application No. PCT/US98/03813, filed on Mar. 23, 1998, now abandoned.
(60) Provisional application No. 60/042,064, filed on Mar. 26, 1997.

(51) Int. Cl.[7] ............................................. A61M 5/178
(52) U.S. Cl. ............................. 604/164.01; 604/170.01
(58) Field of Search .................. 604/164.01, 164.04, 604/164.06, 164.07, 164.08, 164.09, 164.11, 164.12, 164.13, 165.01, 165.02, 165.03, 170.01, 170.02, 158, 164.1, 162, 165.04, 198, 110, 171, 177, 192, 263

(56) References Cited

U.S. PATENT DOCUMENTS

| | | | |
|---|---|---|---|
| 3,491,756 A | 1/1970 | Bentov | ........................ 128/221 |
| 3,727,613 A | * 4/1973 | Sorenson et al. | ......... 128/214.4 |
| 3,809,081 A | 5/1974 | Loveless | .................. 124/214.4 |
| 4,170,993 A | 10/1979 | Alvarez | .................. 128/214 R |

(List continued on next page.)

FOREIGN PATENT DOCUMENTS

| | | | | |
|---|---|---|---|---|
| EP | 0 853 953 A1 | 7/1998 | .......... | A61M/25/06 |
| GB | 2 259 254 A | 3/1993 | ............ | A61M/5/32 |

*Primary Examiner*—Brian L. Casler
*Assistant Examiner*—Jennifer Maynard
(74) *Attorney, Agent, or Firm*—Knobbe, Martens, Olson & Bear, LLP

(57) ABSTRACT

A novel self-blunting needle apparatus (10*d*) employs a blunting member (70) and a needle (12). The blunting member (70) may be disposed within the needle (12) and may be adapted for fluid flow therethrough. The needle (12) may then be inserted into a patient's tissue and the blunting member (70) may be extended to blunt the apparatus. In other embodiments, e.g., apparatus (10), a driver (76) may be employed to move the blunting member (70) without obstructing fluid flow. There may be a locking spline (58) and cam channel (30) configuration to prevent backward motion of the blunting member (70) in various embodiments. A hollow body (22) is configured to facilitate assembly.

34 Claims, 16 Drawing Sheets

U.S. PATENT DOCUMENTS

| | | | |
|---|---|---|---|
| 4,274,408 A | 6/1981 | Nimrod | 128/214.4 |
| 4,525,157 A | 6/1985 | Vaillancourt | 604/52 |
| 4,529,399 A | 7/1985 | Groshong et al. | 604/53 |
| 4,613,329 A | 9/1986 | Bodicky | 604/158 |
| 4,624,243 A * | 11/1986 | Lowery et al. | 128/6 |
| 4,627,841 A * | 12/1986 | Dorr | 604/158 |
| 4,790,828 A | 12/1988 | Dombrowski et al. | 604/198 |
| 4,795,432 A | 1/1989 | Karczmer | 604/110 |
| 4,801,295 A | 1/1989 | Spencer | 604/198 |
| 4,804,371 A | 2/1989 | Vaillancourt | 604/198 |
| 4,808,169 A | 2/1989 | Haber et al. | 604/195 |
| 4,810,248 A | 3/1989 | Masters et al. | 604/192 |
| 4,828,547 A | 5/1989 | Sahi et al. | 604/110 |
| 4,917,669 A * | 4/1990 | Bonaldo | 604/164 |
| 4,978,344 A | 12/1990 | Dombrowski et al. | 604/198 |
| 5,009,642 A * | 4/1991 | Sahi | 604/158 |
| 5,030,205 A | 7/1991 | Holdaway et al. | 604/164 |
| 5,067,946 A * | 11/1991 | Zhadanov | 604/198 |
| 5,176,655 A | 1/1993 | McCormick et al. | 604/198 |
| 5,256,152 A | 10/1993 | Marks | 604/198 |
| 5,370,623 A * | 12/1994 | Kreamer | 604/165 |
| 5,389,085 A | 2/1995 | D'Alessio et al. | 604/198 |
| 5,498,241 A | 3/1996 | Fabozzi | 604/177 |
| 5,501,672 A | 3/1996 | Firth et al. | 604/177 |
| 5,527,284 A | 6/1996 | Ohnemus et al. | 604/110 |
| 5,549,571 A | 8/1996 | Sak | 604/198 |
| 5,562,637 A | 10/1996 | Utterberg | 604/263 |
| 5,578,053 A * | 11/1996 | Yoon | 606/185 |
| 5,582,597 A | 12/1996 | Brimhall et al. | 604/192 |
| 5,685,856 A * | 11/1997 | Lehrer | 604/170 |
| 5,697,914 A | 12/1997 | Brimhall | 604/177 |
| 5,743,882 A * | 4/1998 | Luther | 604/168 |
| 5,755,673 A | 5/1998 | Kinsey | 600/577 |
| 5,951,520 A * | 9/1999 | Burzynski et al. | 604/170 |
| 6,146,337 A * | 11/2000 | Polidoro et al. | 600/576 |
| 6,270,480 B1 | 8/2001 | Dorr et al. | 604/158 |

* cited by examiner

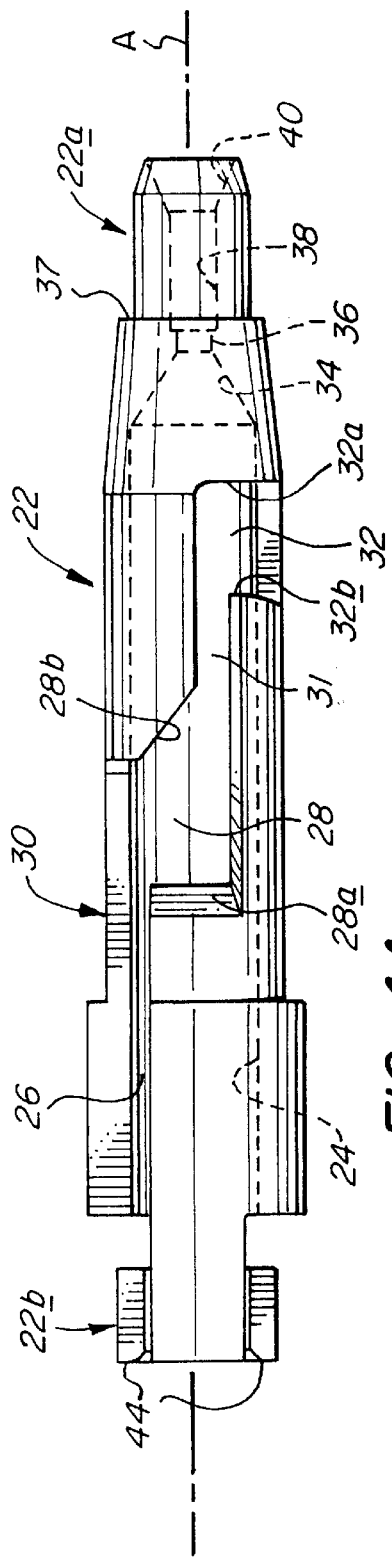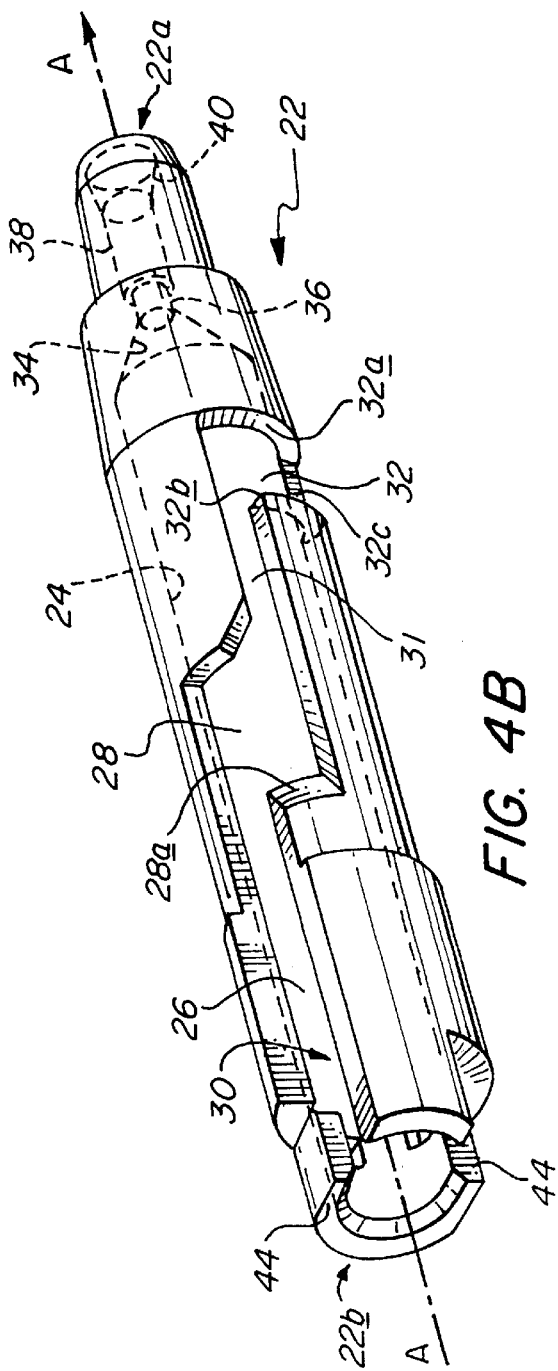
FIG. 4A
FIG. 4B

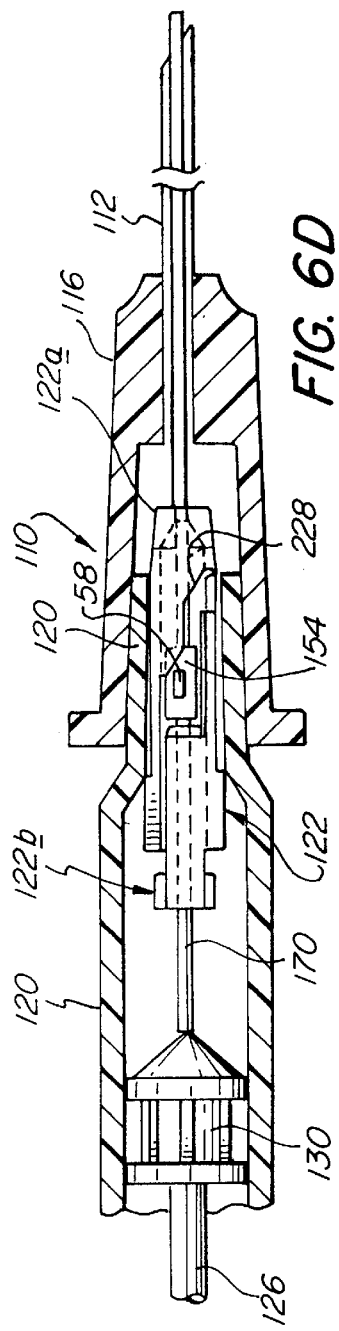
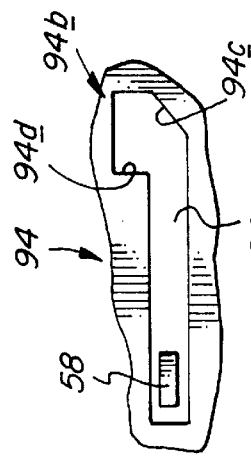
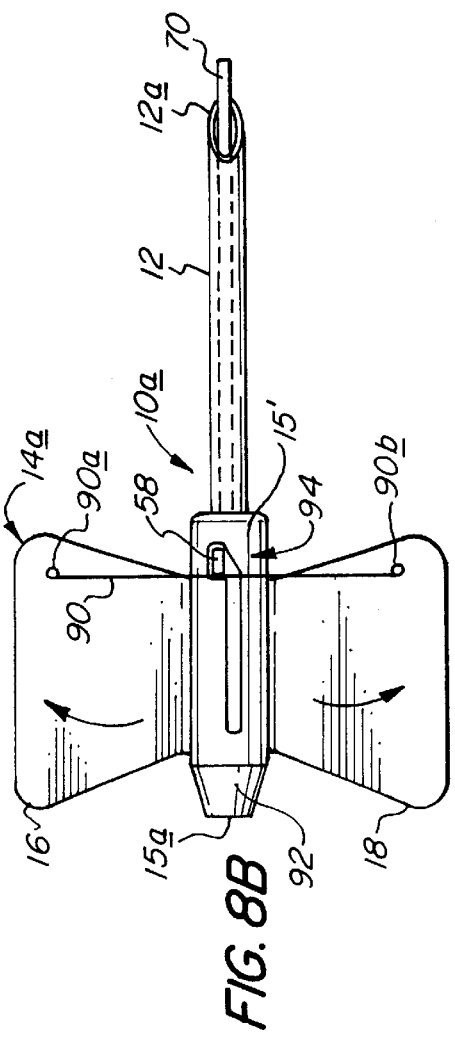
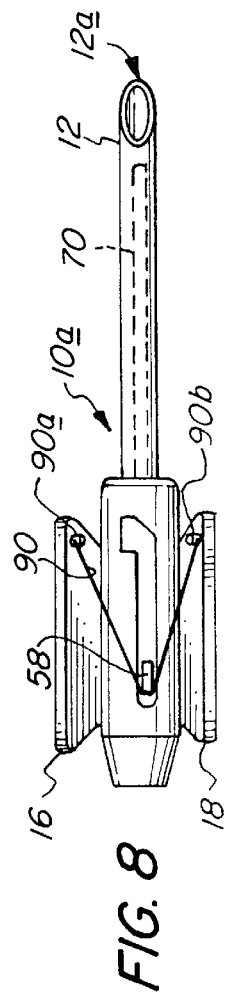

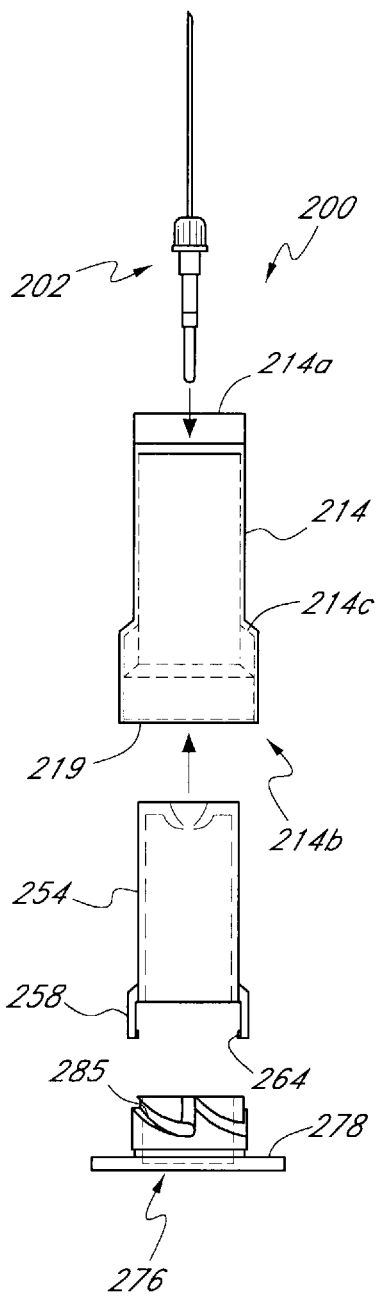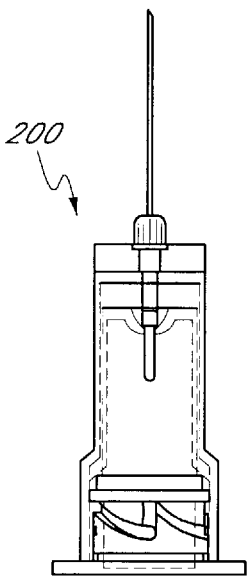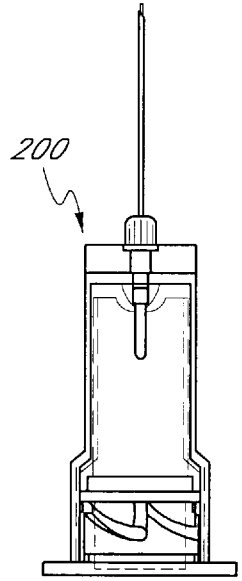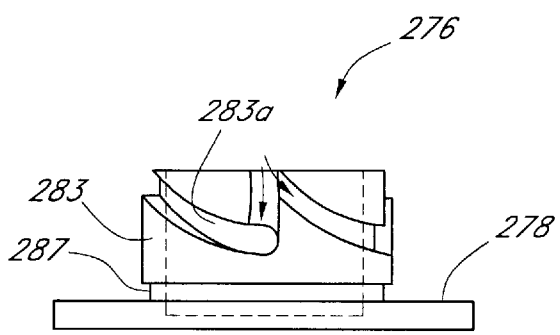
FIG. 7B
FIG. 7E
FIG. 7F
FIG. 7G

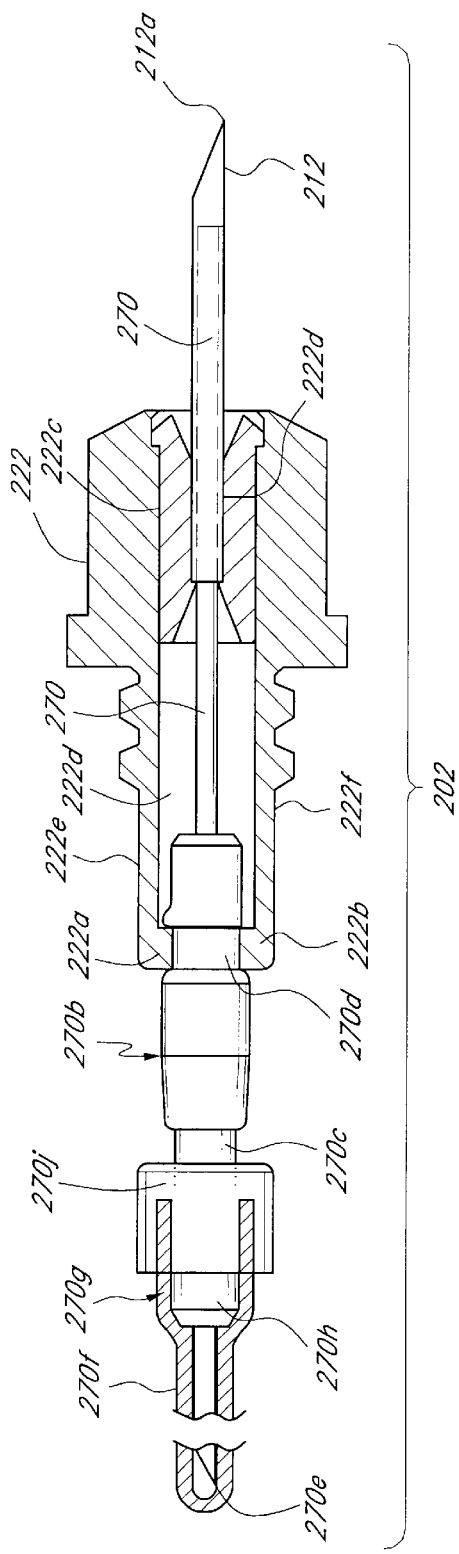
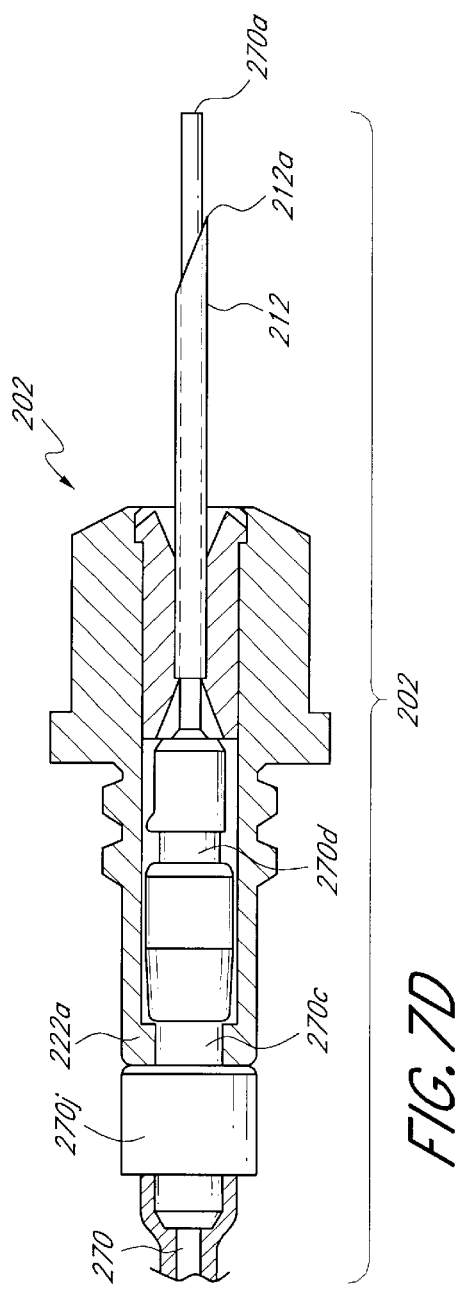
FIG.7C
FIG.7D

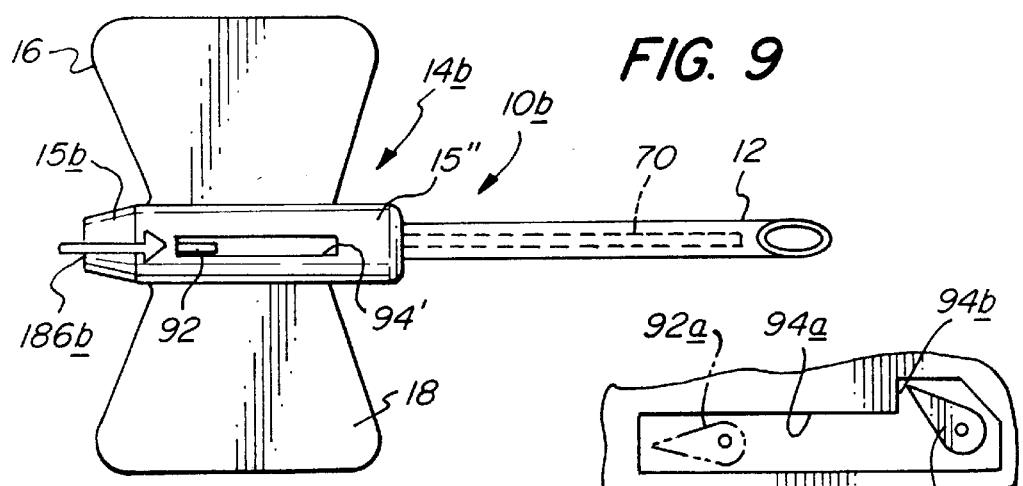
FIG. 9
FIG. 9A
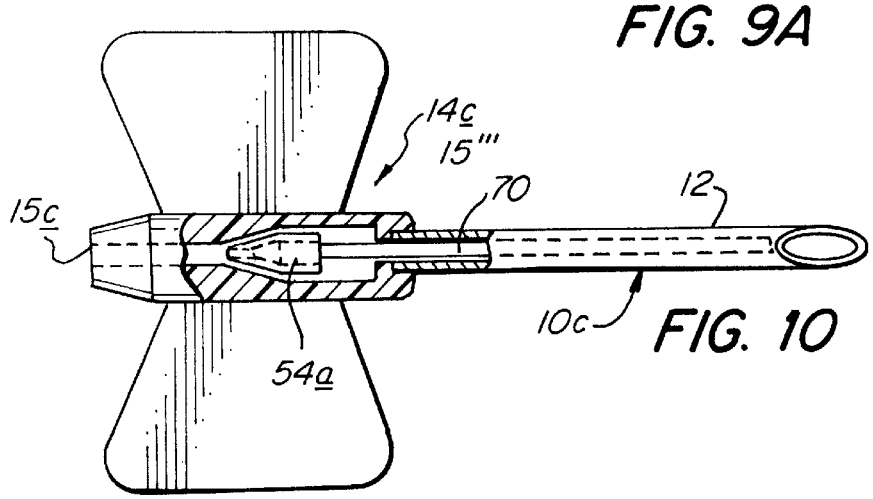
FIG. 10
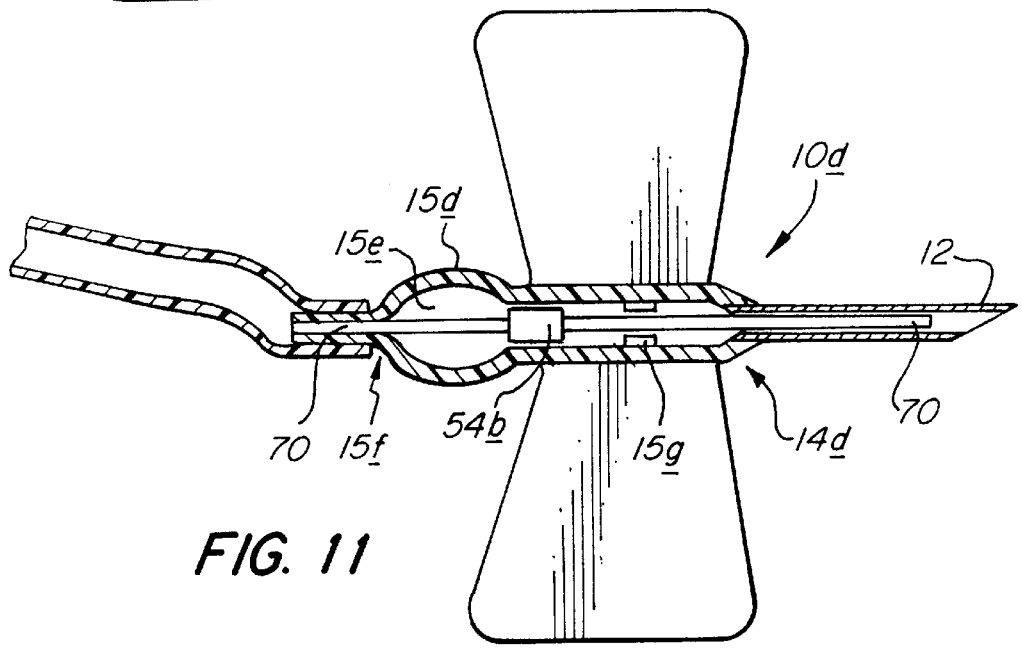
FIG. 11

PARENTERAL FLUID TRANSFER APPARATUS

CROSS-REFERENCE TO RELATED APPLICATIONS

This application is a continuation-in-part and claims priority of co-pending Patent Cooperation Treaty Application PCT/US98/03813, filed Mar. 23, 1998 (now abandoned), which designated the United States and claimed the benefit of U.S. provisional application number 60/042,064, filed Mar. 26, 1997.

BACKGROUND OF THE INVENTION

1. Field of the Invention

The present invention relates to parenteral fluid transfer apparatus having a body member through which fluids are parenterally delivered to and/or withdrawn from a patient (human or animal) through venipuncture or the like. More particularly, this invention is directed to such apparatus having a needle and a self-blunting mechanism.

2. Related Art

For reasons which have received wide publicity, there is substantial demand for self-blunting venipuncture products which may be employed by healthcare workers with minimal risk of incurring accidental needle-stick wounds. A highly successful venipuncture product of this nature is sold under the trademark PUNCTUR-GUARD® by Bio-Plexus, Inc. of Vernon, Conn. The PUNCTUR-GUARD® blood collection needle assembly is manufactured in accordance with the teachings of U.S. Pat. No. 4,828,547, issued on May 9, 1989 to Carl R. Sahi et al, the disclosure of which is hereby incorporated herein by reference. In the PUNCTUR-GUARD® product, a tubular blunting member is disposed within the bore of a needle, i.e., a needle cannula having a conventional beveled tip suitable for penetrating tissue to initiate venipuncture. The blunting member and needle combination of the syringe is initially in an insertion configuration, in which the tissue puncture tip of the needle extends beyond the blunt tip of the blunting member, so normal penetration of the needle into tissue is not affected. The user takes a conventional finger and thumb grip on the barrel finger rest and plunger thumb rest to manipulate the needle. After venipuncture has been achieved, but prior to removal of the needle from the patient, the user advances the syringe plunger relative to the needle by applying thumb and finger pressure to the thumb and finger rests, thus advancing the blunting member so that the tip of the blunting member extends beyond the tissue-penetrating tip of the needle. In this extended configuration of the blunting member and needle combination, the needle tip is effectively blunted to thereby prevent accidental needle-stick wounds upon or after removal of the needle from the patient. Such an arrangement offers the advantages of being economical, reliable and simple in construction and in use.

Another known, commercially available device that makes use of a self-blunting needle assembly is a blood collection needle. The needle assembly comprises a needle cannula mounted in a hub. The hub is configured to engage a standard blood collection tube holder. The assembly comprises a blunting component that comprises a hub having a tubular member extending therethrough. One portion of the tubular member (referred to as the blunting member) extends from the blunting component hub, terminates with a blunt end, and is configured to be slidably received within the needle cannula. The other end of the tubular member extends from the blunting component hub in the opposite direction and terminates with a puncture tip for puncturing the seal on a conventional blood collection vial. The blunting component hub slidably engages the needle component hub and is movable from a retracted position in which the blunt end of the tubular member is within the needle cannula, placing the assembly in a sharpened, insertion configuration, to an extended position in which the blunt end of the tubular member extends beyond the tip of the needle cannula, thus blunting the needle and placing the assembly in a blunted configuration. A groove and detent arrangement between the needle hub and the blunting component hub secures the assembly in the blunted configuration. The assembly is secured in the holder in the insertion configuration. The user grasps the collection tube holder to insert the needle cannula into a patient's vein. Then, a blood collection tube is inserted into the holder and the puncture tip of the tubular member penetrates the seal on the vial, permitting blood to flow into the tube. To blunt the needle, the user pushes the collection vial further into the holder, causing the seal to bear upon the blunting component hub and to advance the blunting component into the extended position to blunt the needle assembly.

The art shows attempts to reduce the accidental needle-stick danger associated with the use of other medical sharps as well, often by the use of exterior sheathing devices such as that of McCormick et al, U.S. Pat. No. 5,176,655. Other medical sharps devices employing needle-sheathing devices are illustrated by Dombrowski et al U.S. Pat. No. 4,790,828; Dombrowski et al U.S. Pat. No. 4,978,344; Vaillancourt U.S. Pat. No. 4,804,371; and Karczmer U.S. Pat. No. 4,795,432.

U.S. Pat. No. 4,627,841 to Dorr, issued on Dec. 9, 1986, discloses an infusion needle having a needle mounted in a hub and a hollow blunting member mounted in a hub and being telescopically received within the needle. A spring pulls the hubs together, causing the forward end of the blunting member to extend beyond the needle tip. The rearward end of the blunting member is secured to a tube or other fluid flow device. The device comprises wings that carry wedges and that are folded towards each other to provide a haft by which the user manipulates the needle. When the wings are folded towards each other, the wedges are driven between the needle hub and the blunting member hub, thereby separating the hubs by overcoming resistance of the spring and causing the blunting member to retract into the needle.

SUMMARY OF THE INVENTION

Generally, the present invention overcomes the above-discussed and other deficiencies and disadvantages of the prior art by providing novel and improved parenteral fluid flow apparatuses for subcutaneous delivery of fluids to, and/or withdrawal of fluids from, a patient.

One broad aspect of the present invention provides a needle apparatus comprising a cannula component comprising a needle cannula and a blunting member. The needle cannula has a longitudinal axis, a puncture tip, and a needle passageway therethrough, and the blunting member has a blunt end. The needle cannula and the blunting member are disposed telescopically one within the other and are configured for movement (i) from an insertion configuration in which the puncture tip of the needle cannula extends beyond the blunt end of the blunting member, (ii) to a blunted configuration in which the blunt end of the blunting member extends beyond the puncture tip to blunt the apparatus. There is a haft connected to the cannula for use in manipulating the cannula component, and an oblique motion deployment means for moving the apparatus from the insertion configuration to the blunted configuration independently of the function of the haft means.

A needle apparatus in accordance with the present invention may have a fluid flow passageway therethrough and may comprise a needle component having a needle component passageway therethrough and comprising a hub portion and a needle cannula, the needle cannula having a longitudinal axis and being joined to, and extending from, the hub portion and having a proximal end and a puncture tip. There is also a blunting component comprising a blunting member having a proximal end and a blunt distal end, the blunting component being dimensioned and configured to be received in the needle component passageway. The blunting component and the needle component are movable relative to each other from an insertion configuration, in which the puncture tip of the needle cannula extends beyond the blunt end of the blunting member, to a blunted configuration, in which the blunt distal end of the blunting member protrudes beyond the puncture tip of the needle cannula, thus blunting the needle cannula. There is an oblique motion deployment means for moving the apparatus from the insertion configuration to the blunted configuration, and a haft connected to the needle component for use in manipulation of the needle cannula without moving the apparatus from the insertion configuration to the blunted configuration.

According to one aspect of the invention, the oblique motion deployment means may comprise a screw thread engagement between the blunting component and the needle component. Alternatively, the oblique motion deployment means may comprise a pliant portion of the needle component configured to be compressible by the user. The blunting component may be dimensioned and configured to move from the insertion configuration to the blunted configuration upon compression of the pliant portion of the needle component. Optionally, the apparatus may comprise a fluid flow passageway therethrough and the pliant portion may comprise a working fluid reservoir, the working fluid being isolated from the fluid flow passageway, and wherein the deployment means comprises a piston and cylinder engagement of the blunting component and the needle component.

According to another aspect of the invention, an apparatus may comprise deployment means comprising a drive member in articulated connection with at least one, optionally both, of the blunting component and the needle component. For example, the drive member may rotatably engage the needle component. Optionally, the drive member is rotatable about an axis that is aligned with the longitudinal axis of the needle cannula. In one embodiment, the blunting component may comprise a shuttle portion and the drive member may comprise a cam surface that bears upon the shuttle portion. The apparatus may be configured to permit the shuttle portion to serve as a cam follower to move the apparatus from the insertion configuration to the blunting configuration in response to rotation of the drive member relative to the needle component. Alternatively, the drive member may be rotatable about an axis that is disposed transversely to the longitudinal axis of the needle cannula.

In another embodiment, the drive member may comprise a contrary motion linkage between the blunting component and the needle component such as a lever or a diverted tension line.

In a particular embodiment, the deployment means may comprise a stored energy means and a release mechanism.

According to another aspect of this invention, the apparatus may comprise locking means for locking the apparatus in the blunted configuration. The locking means may comprise a spline and cam channel engagement between the blunting component and the needle component.

In some embodiments, the apparatus comprises a blunting component and the needle component disposed in a tandem configuration wherein the blunting component defines the proximal aperture of the apparatus. In other embodiments, the drive member is disposed in tandem relation to the needle component and defines the proximal aperture of the apparatus. In still other embodiments, the needle component defines the proximal aperture of the apparatus.

In one particular embodiment, the apparatus may comprise a pair of wings that are connected to the needle component. The wings may be displaceable about a displacement axis that is aligned with the longitudinal axis of the needle cannula and may be movable between a manipulation position and a neutral position. There may be a tension line secured to the wings and connected to the blunting component, the tension line being configured so movement of the wings from the manipulation position to the neutral position causes the tension line to move the apparatus from the insertion configuration to the blunted configuration.

Another broad aspect of this invention provides a needle apparatus comprising a needle component comprising a hub portion and a needle cannula, the needle cannula being joined to, and extending from, the hub portion and having a proximal end and a puncture tip, and defining a longitudinal axis, the hub portion and the needle cannula cooperating to define a needle component passageway for fluid flow therethrough. There is a blunting component comprising a blunting member having a blunt distal end and a proximal end, the blunting member being disposed in coaxial relation to the needle cannula. The blunting component and the needle component are movable relative to each other from an insertion configuration, in which the puncture tip of the needle cannula extends beyond the blunt end of the blunting member, to a blunted configuration, in which the blunt distal end of the blunting member protrudes beyond the puncture tip of the needle cannula, thus blunting the needle cannula. The apparatus includes locking means comprising a spline and a cam channel, for locking the apparatus in the blunted configuration.

In one embodiment, the cam channel may comprise a catch portion, the apparatus comprising catching means for moving the spline into the catch portion of the channel. The catching means may comprise a slide surface in the cam channel. Optionally, the blunting component may comprise a driving means for engaging the needle component and the blunting member and for moving the apparatus from the insertion configuration to the blunted configuration.

Still another broad aspect of this invention provides a needle apparatus having a fluid flow passageway therethrough extending from a first aperture to a second aperture comprising a needle component comprising a needle cannula mounted on a needle hub and a blunting member mounted on a blunting member hub. The needle cannula comprises a puncture tip that defines the first aperture of the apparatus. The needle component and the blunting member component are configured to be received one within the other to provide an outer component and an inner, movable component. The blunting component and the needle component are movable between an insertion configuration in which the tip of the needle extends beyond the blunt end of the blunting member to a blunted configuration in which the blunt tip extends beyond the needle tip to obscure the needle tip and thus blunt the apparatus. The outer component defines the second aperture of the apparatus and further comprises an access aperture. The inner component comprises a lug that protrudes through the access aperture for manipulation by the user to permit the user to move the apparatus from the insertion configuration to the blunted configuration.

Another aspect of this invention relates to a needle apparatus comprising (a) a body member having a longitudinal axis, a proximal end and a distal end, and a longitudinal body passageway extending therethrough and connecting the proximal end and the distal end of the body member in fluid flow communication with each other; (b) a cannula component carried on the body member and disposed therein in fluid flow communication with the body passageway, the cannula component comprising a needle member and a blunting member, the needle member having a tissue puncture tip and a needle proximal end, and the blunting member having a blunting tip and a blunting member proximal end, the needle member and the blunting member being arranged with their respective tips facing in the same direction, and telescopically one within the other for relative axial movement of the needle member and the blunting member from (i) an insertion configuration of the cannula component, in which the puncture tip extends beyond the blunting tip, to (ii) a blunted configuration of the cannula component, in which the blunting tip extends beyond the tissue puncture tip to blunt the same; (c) a shuttle member mounted for axial movement within the body passageway, the shuttle member (1) being dimensioned and configured to provide a first fluid flow passageway extending therethrough, and (2) engaging one of the blunting member and the needle member whereby axial movement of the shuttle member causes axial movement of the blunting member and needle member relative to each other to change the cannula component from its insertion configuration to its blunted configuration; and (d) a drive member in the body passageway which (1) is manipulable from exteriorly of the body member, (2) is dimensioned and configured to leave the body passageway open to fluid flow between the proximal and distal ends of the body member, and (3) is operatively connected to the shuttle member, whereby manipulation of the drive member moves the shuttle member axially through the body passageway, thereby changing the cannula component from its insertion configuration to its blunted configuration, without significant hydraulic effect on biologic fluid in the apparatus.

The drive member may comprise a cam surface and the shuttle may comprise a following surface. The apparatus may further comprise an actuator connected to the drive member and accessible for manipulation thereof from exteriorly of the body member, the drive member (1) being mounted for rotation within the body passageway, (2) being rotatable therein by manipulation of the actuator, and (3) operatively engaging the shuttle member, wherein manipulation of the actuator rotates the drive member to impose force on the following surface via the cam surface to move the shuttle member axially along the body passageway, thereby changing the cannula component from its insertion configuration to its blunted configuration. In a particular embodiment, the needle member may be mounted on the body member and the blunting member may be mounted on the shuttle member and may be disposed telescopically within the needle member.

There may be locking means comprising a spline member and cam channel engagement of the blunting component and the needle component, the cam channel comprising an axially extending guide channel and a catch portion that connects with the guide channel at a lateral channel entryway, and the catch portion extending transversely of the guide channel and comprising a backward stop surface;

wherein the spline member is dimensioned and configured to traverse the guide channel as the blunting component moves from the insertion configuration to the blunted configuration; and wherein the following surface of the shuttle member and the cam surface of the drive member are each dimensioned and configured so that rotation of the drive member in one direction advances the spline member along the guide channel and into the catch portion for engagement therewith, and rotation of the drive member in the opposite direction effectively disengages the cam follower and the cam surface, thereby locking the apparatus in the blunted configuration.

There may be an air- and liquid-tight sealant sheath disposed over the body member.

Yet another aspect of the invention relates to a needle apparatus comprising a hollow body, the body having a proximal end and a distal end and defining a cavity extending along a body axis from the proximal end to the distal end of the body. The cavity includes a first generally conical region disposed at the distal end of the body, a first generally cylindrical region coaxially disposed adjacent the first conical region, a second generally cylindrical region coaxially disposed adjacent the first cylindrical region, a second generally conical region coaxially disposed adjacent the second cylindrical region and a third generally cylindrical region coaxially disposed adjacent the second conical region and extending therefrom to the proximal end of the body, the diameter of the second cylindrical region being less than that of the first cylindrical region and the diameter of the third cylindrical region being greater than that of the second cylindrical region. There is a cannula having a forward end and a terminal end, the outer diameter of the cannula being substantially equal to the diameter of the first cylindrical region of the cavity, the terminal end of the cannula being received within the, first cylindrical region such that the forward end extends forwardly of the distal end of the body and the cannula extends along the body axis. There is also a movable member means being at least partially disposed within the body cavity and having a forward end and an outer diameter which is not greater than either of the inner diameter of the cannula or the diameter of the second cylindrical region of the cavity, the movable member extending through the second cylindrical region of the cavity and being at least partially movably received within the cannula. One of the forward end of the cannula the forward end of the movable member having a tissue puncture tip and the other of the forward end of the cannula or the forward end of the movable member having a blunt tip.

The locking means of the foregoing devices may optionally comprise a detent on one of the needle component and the blunting component, and a ramp on the other. The ramp may define a shoulder, and the detent is positioned and configured to ride up the ramp as the blunting member is advanced to be positioned to bear against the shoulder to inhibit rearward movement after the blunted configuration is attained.

Independently, the locking means may comprise a detent and an axially-extending slot arrangement wherein the detent is positioned and configured to move axially in the slot as the blunting member is advanced. The slot may be configured to define a pinch region through which the detent passes, the pinch region being configured to inhibit entry of the detent into the slot once the blunted configuration is attained.

In either case, there may optionally be a return ramp for permitting the detent to move axially past the shoulder so that the apparatus can return to the sharpened configuration.

Any of the foregoing embodiments may comprise locking means, optionally comprising a spline and cam channel, for locking the apparatus in the blunted configuration.

BRIEF DESCRIPTION OF THE DRAWINGS

The present invention will be described below with reference to the accompanying drawings, wherein:

FIG. 4A is a side elevation view of the body member of the apparatus depicted in FIG. 2;

FIG. 4B is a perspective view of the body member of the apparatus depicted in FIG. 2;

FIG. 6D is a partly cross-sectional view of a syringe comprising the locking spline and cam channel engagement of a blunting component and a needle component in accordance with one aspect of the present invention;

FIG. 7B is an exploded view of a blood collection needle in accordance with various aspects of the present invention;

FIGS. 7C and 7D are elevational views of the self-blunting needle assembly used in the blood collection needle of FIG. 7B shown in the blunted and sharpened configurations, respectively;

FIG. 7E is an elevation view of the driver of the blood collection needle of FIG. 7B;

FIGS. 7F and 7G are schematic illustrations of the assembled blood collection needle of FIG. 7B in the sharpened and blunted configurations, respectively;

FIGS. 8 and 8B are plan views, and FIG. 8A is an enlarged partial plan view of a blunting apparatus comprising a tension line for deploying the blunting member and a lug and access slot locking means;

FIG. 9 is a plan view of a needle apparatus in which the internal blunting member has a lug that protrudes through an access slot in the needle member;

FIG. 9A is a plan view of a rotatable lug for use in a catch slot locking means;

FIG. 10 is a partially cross-sectional plan view of a needle apparatus having a pliant external member for moving the internal member;

FIG. 11 is a partially cross-sectional plan view of a needle apparatus having a piston deployment means for moving the blunting member;

DETAILED DESCRIPTION OF THE INVENTION AND PREFERRED EMBODIMENTS THEREOF

Figure 1:
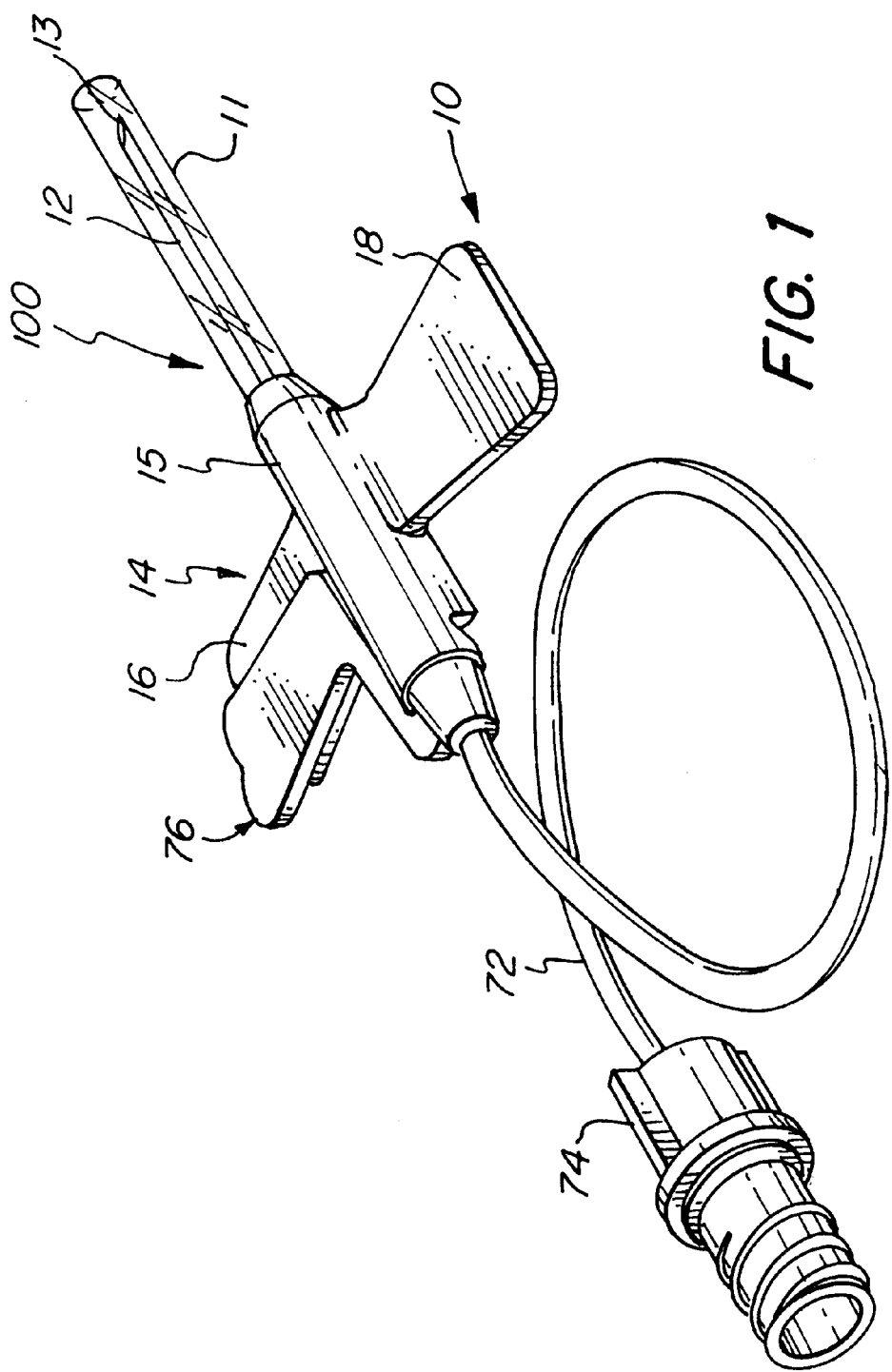
FIG. 1 is a perspective view of a winged set comprising a parenteral flow transfer apparatus in accordance with one embodiment of the present invention in combination with associated components comprising a protective casing, a fluid transfer tube and a female luer adapter.

The present invention provides parenteral fluid transfer apparatuses (or "needle apparatuses") for medicinal use which can be blunted during use and which preferably (but not necessarily) permit fluid flow therethrough even while blunted. Typically, the fluid flowing through the apparatus is either a medicinal fluid being administered to a patient or a metabolic fluid (e.g., blood) being withdrawn from the patient. Such fluids are referred to collectively herein as "biologic fluids". As will be discussed below, the term "needle apparatus", as used herein, encompasses various needle devices such as, for example, wing sets, blood collection needles, syringes and catheters.

A needle apparatus in accordance with one principal aspect of this invention comprises a cannula component comprising a needle cannula and a blunting member disposed telescopically one within the other. The longitudinal axis of the needle cannula defines the axis of the apparatus. Typically, the blunting member and the needle cannula each carry a hub in which they are mounted, and together with which they comprise a blunting component or needle component, respectively. Since the blunting member and the needle cannula are disposed telescopically one within the other, one of the blunting component and the needle component constitutes an inner component and the other constitutes an outer component. The member comprising part of the inner component (most often illustrated herein as the blunting member) is sometimes referred to herein as the moving member. Whatever their relative configurations, the needle cannula has a sharp puncture tip at its distal or forward end (i.e., the end directed towards the patient by another (referred to herein as the "user") when the needle is inserted) and the blunting member has a blunt tip at its forward end. The needle cannula and the blunting member are movable relative to each other from an insertion or sharpened configuration, in which the sharp tip of the needle cannula extends beyond the blunt end of the blunting member, to a blunted configuration, in which the forward blunt end of the blunting member extends beyond the sharp tip of the needle cannula and thus blunts the needle cannula of the apparatus. In particular embodiments of this invention, the cannula component can be blunted and still permit the flow of fluid therethrough. Such embodiments may be described as comprising a non-obstructive blunting member, i.e., a blunting member that is either disposed outside the needle cannula or one that is disposed inside the needle cannula (an "internal"blunting member) but that permits fluid flow therethrough nonetheless. A non-obstructive internal blunting member may allow fluid to flow around it within the needle cannula, through it, or both. An obstructive blunting member obturates the needle cannula and substantially stops fluid flow therethrough.

Some apparatuses according to the present invention comprise an oblique motion deployment means for changing the configuration of the apparatus at least from an initial insertion configuration to a blunted configuration. The oblique motion deployment means permits the user to effect relative axial movement between the blunting component and the needle component without applying a direct axial force to one or the other. Rather, the oblique motion deployment means allows the user to effect such relative axial movement by applying an oblique motion, optionally by manipulating an intermediate structure (referred to herein as a drive member) joined to both the blunting component and the needle component. In various embodiments, the oblique motion may be achieved by applying radial, lateral or rotational force rather than a substantially directly forward or rearward axial force to the appropriate structure of the apparatus. By allowing the user to avoid applying direct axial force on the apparatus, the oblique motion deployment means reduces the risk that the user might inadvertently impose a jarring motion on the needle that would drive the needle deeper into the injection site than is necessary or desired.

Certain aspects of this invention are disclosed herein as pertaining to flow-through devices such as winged needle apparatuses which are designed to permit attachment to generic fluid handling devices such as tubing or a luer connector. Some such aspects of the invention might therefore not pertain to more specialized devices such as syringes or blood collection needles, in which the connectivity issues are more limited.

In various embodiments, e.g., some winged needle apparatuses and blood collection needles, the deployment means may operate without significantly affecting the flow of fluid through the apparatus, i.e., without significant hydraulic effect on biologic fluid in the flow passageway of the apparatus. Thus, the blunting component may be deployed without requiring or causing biologic fluid to flow through the apparatus, or without interfering with such flow. The mere effect, if any, of friction between the biologic fluid and a moving non-obstructive blunting member in contact therewith is not a significant hydraulic effect for purposes of this invention.

An apparatus in accordance with the present invention typically comprises a haft to facilitate handling of the needle cannula by the user for the purpose of effecting venipuncture. The haft can take a variety of forms, such as the wings of a winged needle apparatus, the thumb and finger rests on a hypodermic syringe, or even the sides of a body in which the needle is mounted. The haft of a winged needle apparatus typically comprises a pair of resilient wings that normally lie in a common plane, but which are bendable, i.e., displaceable. The user may bend the wings out of their common plane and pinch them together between the thumb and forefinger in a manipulation position, thus providing a convenient means for handling the cannula component and for inserting the needle where required.

In certain embodiments of the present invention, the displacement of the haft, e.g., the bending of the wings, will not force the deployment means to change the device between its blunted and insertion configurations. In other words, the oblique motion deployment means of the present invention may be operable independently of the user's employment of the haft, i.e., independently of the user's grasp on the device to manipulate and insert the needle. Such embodiments may be described as comprising non-deploying haft, to identify the distinction over, e.g., the Dorr Patent, U.S. Pat. No. 4,627,841, discussed above. In other embodiments, displacement of the wings (or other haft means) may change the configuration of the apparatus.

In some embodiments of this invention, the needle component will encompass the entire flow passageway of the apparatus, providing a forward or distal aperture at the tip of the needle at one end and a rearward or proximal aperture at the opposite end, with the fluid flow passageway of the apparatus extending therebetween. In other embodiments, two or more components may each define a flow aperture and may be disposed in tandem to each other so that the fluid flow passageway of the apparatus extends from one component to the next. For example, the blunting component may comprise a hollow blunting member within the needle cannula and may sealingly engage the interior of the needle component. The blunting component, however, may protrude from the proximal end of the needle component passageway and may define the proximal aperture of the device (to which, e.g., a luer adapter may be connected) and the fluid flow passageway may extend from the proximal aperture to the needle tip. In other embodiments, a drive member may define the proximal aperture and may sealingly engage the needle component or the blunting component in a tandem configuration therewith.

Various embodiments of this invention may comprise a drive member that is rotatable relative to one or both of the needle cannula and the blunting member. The drive member may be rotatable about an axis that is aligned with (i.e., substantially parallel with) the longitudinal axis of the needle cannula or along an axis that is disposed transversely, preferably substantially perpendicular, to it. In various other embodiments, the drive member may comprise a lever, a tension line, a stored energy mechanism or a contrary motion mechanism.

As mentioned above, in the preferred embodiments of this invention, the blunting member is deployed from within the needle, so the device can be blunted after insertion into tissue but before the needle is withdrawn, i.e., while the needle is in the patient and fluid is flowing therethrough, without any need to withdraw the needle or to disrupt the tissue surrounding the needle, as would be required with the prior art device as shown in U.S. Pat. No. 5,176,655. By blunting the needle while it is in the patient, risk to the user is reduced by obviating the need to expose the puncture tip upon removal of the needle, and the patient is protected against post-insertion injury that may be caused by inadvertent jostling of the needle. Thus, winged needle apparatuses in accordance with the present invention may be safely employed in many situations where standard intravenous catheters (which are blunt) were previously preferred.

The various embodiments of the invention can include any suitable locking means to inhibit the inadvertent retraction of the blunting member from the blunted configuration to the insertion configuration. However, the present invention also provides novel locking means that can be employed with a variety of needle apparatuses. One embodiment of the novel locking means comprises a spline and cam channel engagement between the needle component and the blunting component of the device. As will be described below, the spline and cam channel engagement permits the blunting component to move from an insertion configuration, in which the blunting component is withdrawn, to a blunted configuration, in which the blunting component extends beyond the tip of the needle and thus blunts the device. However, the spline and cam channel engagement inhibits the blunting component against a return motion that would otherwise move the blunting component towards its retracted position to place the device back in the insertion configuration. In addition, if the device comprises a driver for moving the blunting component, the driver may be dimensioned and configured to disengage from the blunting component after the blunted configuration is achieved. Other locking mechanisms may be employed as well, as discussed below. Still other embodiments of this invention relate to needle apparatuses that comprise a hollow body that facilitates the assembly of the apparatus with one component telescopically received in another. These and other aspects of the invention will now be described herein with reference to the Figures.

One embodiment of a parenteral fluid transfer apparatus ("needle apparatus") according to the present invention comprises a self-blunting winged needle apparatus 10, shown in FIG. 1, having a needle 12, a winged body 14, and a winged driver 76.

The apparatus 10 is shown as part of a winged set 100 that comprises a protective sheath 11 disposed around needle 12 and a connector comprising a collection tube 72 and a conventional female luer adapter 74. (Sheath 11 and the connector are not, per se, part of the invention.) Sheath 11 is a conventional sheath which is provided to prevent damage to needle 12 during shipping. Adapter 74 may be fitted to other devices such as a syringe, a fluid reservoir or the like. Apparatus 10 is, therefore, capable of cooperating with tube 72 and adapter 74 to provide a fluid flow passageway therethrough to achieve fluid transfer between a patient and a hypodermic needle or any of the many other similar well-known devices having a fluid reservoir. Winged body 14 preferably includes a central member 15 with first and second wings 16 and 18, respectively, extending from opposite sides of member 15. Needle 12 is mounted in and is oriented coaxially with central member 15 such that a puncture tip 13 of needle 12, which comprises a puncture tip, is directed forwardly of central member 15 with a beveled end thereof facing upwardly. The wings 16, 18 are connected to needle 12 via central member 15 and can be folded upward, together, to provide a convenient haft by which a user can manipulate the needle 12 which, as described below, is part of the cannula component of the apparatus.

Figure 2:
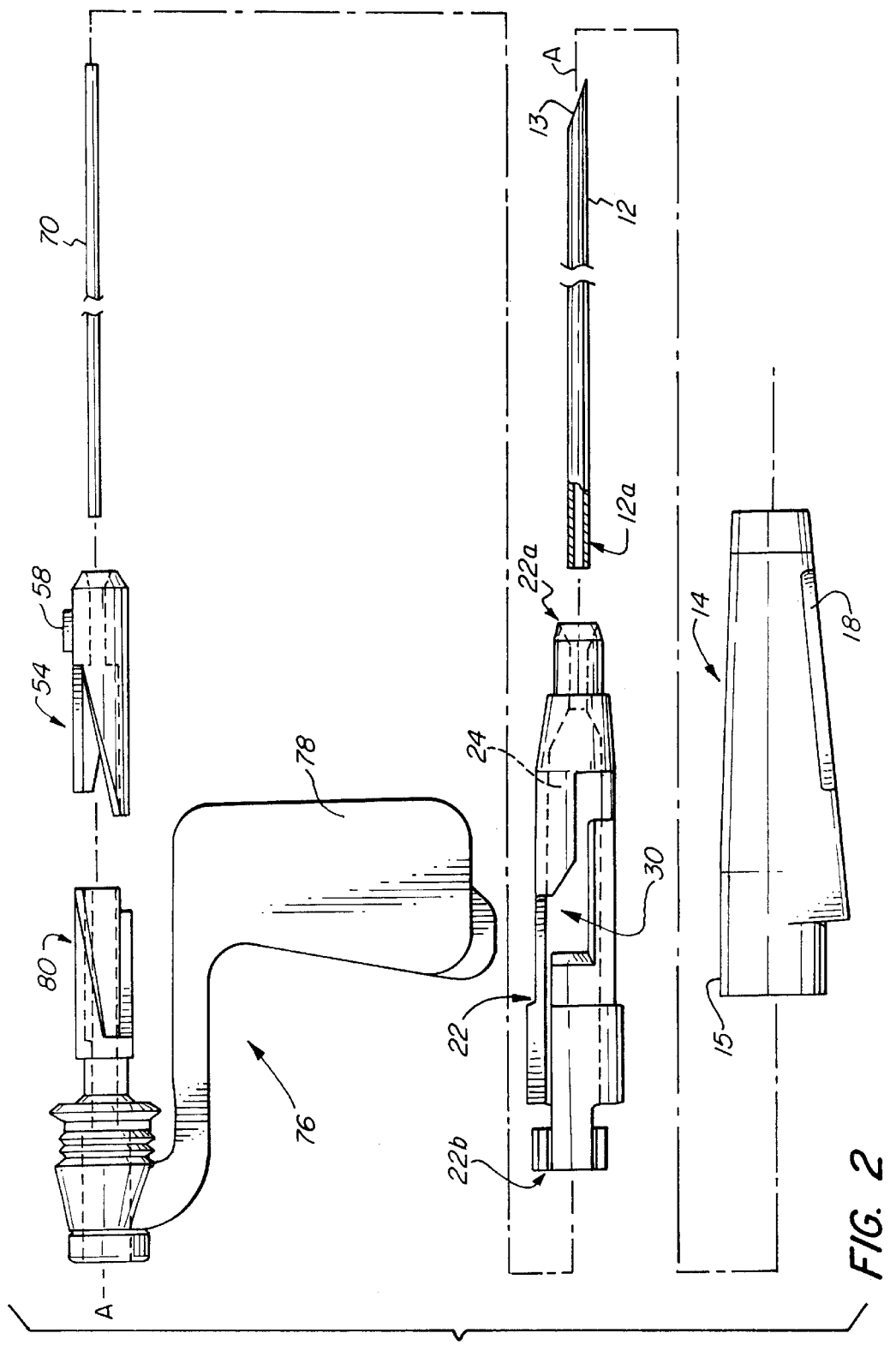
FIG. 2 is an exploded, side elevation view of the components of the apparatus of FIG. 1, excluding the associated components shown in FIG. 1.
Figure 3:
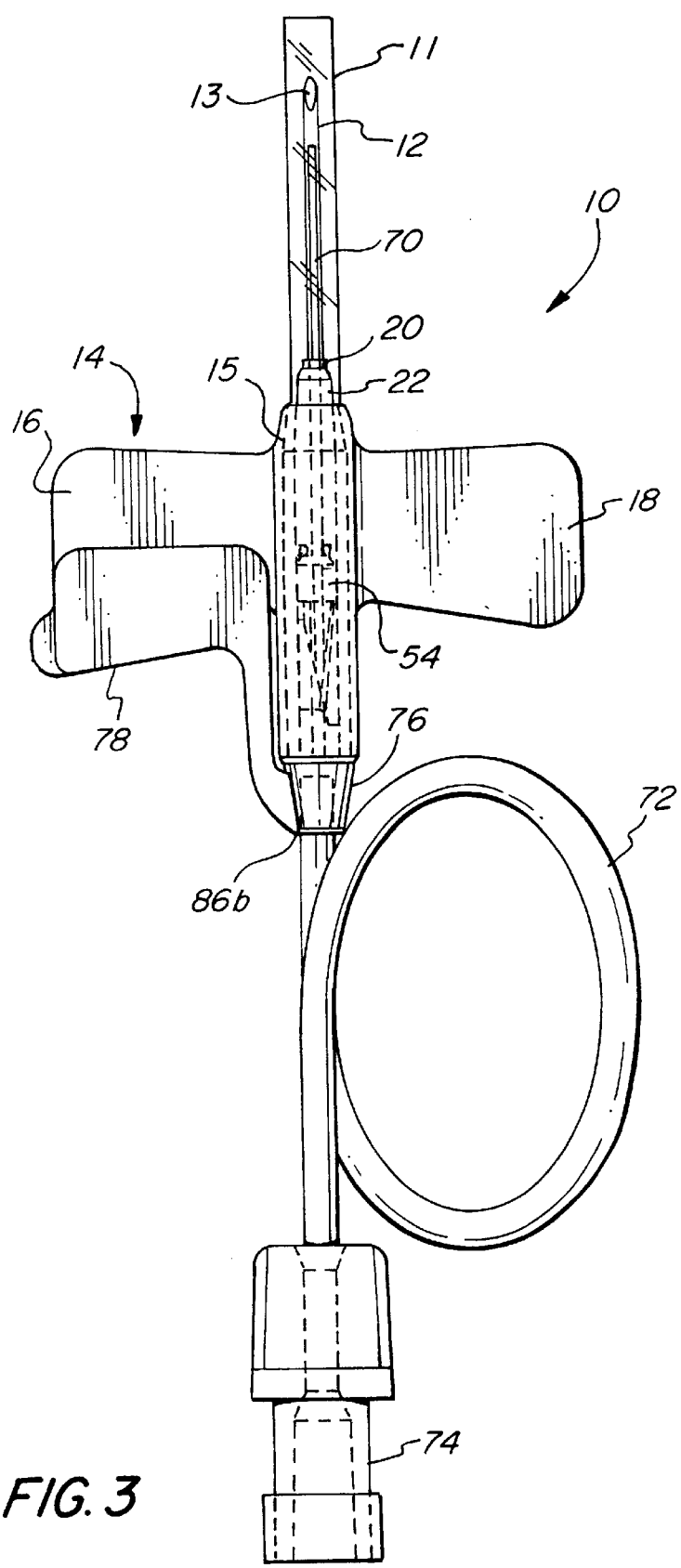
FIG. 3 is a top plan view, partly in cross section, of the apparatus and associated components depicted in FIG. 1.

Referring now to FIG. 2 and FIG. 3, needle 12 has a longitudinal axis A—A and a proximal end 12a (FIG. 2) that is preferably fixed to a distal end 22a of a hollow body 22 with a needle adhesive 20 (FIG. 3) such that needle 12 extends coaxially forward of the distal end 22a of hollow body 22. Together these structures comprise a hub portion in which needle 12 is mounted. The hub portion and needle together comprise the needle component of the apparatus. The cylindrical central member 15 of winged body 14, the cavity 24 in hollow body 22 and needle 12 cooperate to define a needle component passageway therethrough, through which biologic fluids may flow.

FIGS. 4A and 4B depict hollow body 22 in side elevation and perspective views with the hidden details of cavity 24 shown in phantom. As shown therein, hollow body 22 is generally in the form of a hollow cylinder having cavity 24 extending therethrough and defining a body axis that will coincide with longitudinal axis A—A. At distal end 22a of hollow body 22, cavity 24 converges into a plurality of coaxially disposed regions sized and shaped to facilitate assembly of apparatus 10. In particular, beginning at distal end 22a, cavity 24 is bounded by a frusto-conical needle insertion funnel 40. Immediately adjacent funnel 40, cavity 24 is bounded by a cylindrical region 38 with a diameter which is substantially equal to the outer diameter of needle 12. Immediately adjacent cylindrical region 38, cavity 24 takes the form of a blunting member passageway defined by cylindrical region 36. Since the diameter of cylindrical region 36 is less than that of cylindrical region 38, the junction between cylindrical regions 36 and 38 defines a hollow circular wall therebetween. Immediately adjacent cylindrical region 36, cavity 24 is bounded by a frusto-conical blunting member insertion funnel 34. The remainder of cavity 24 is dimensioned and configured to permit shuttle 54 to travel therethrough, and to receive and permit the rotation therein of cam member 80 of driver 76. As best illustrated in FIG. 4B, hollow body 22 comprises a pair of oppositely disposed driver lock tabs 44 at its proximal end. Tabs 44 protrude slightly into cavity 24 and thereby provide a flexible interference fit between hollow body 22 and shuttle 54 and driver 76 (FIG. 2) upon their insertion into cavity 24, as will be described below.

Cavity 24 of body 22 opens radially into a cam channel 30 which is a composite of a plurality of channels that are sized and shaped to cooperate with a spline 58 (FIG. 2) extending from shuttle 54, as will be described below. Cam channel 30 is comprised of an insertion channel 26, a first lateral channel 28, a guide channel 31 and a second lateral channel 32. Insertion channel 26 is open at the proximal end 22b of body 22 and has a linear configuration that runs substantially parallel to axis A—A; first lateral channel 28 extends radially about axis A—A and is bounded by a stop surface 28a disposed in perpendicular relation to axis A—A and a slide surface 28b which has an oblique disposition relative to axis A—A and which extends towards distal end 22a. Lateral channel 28 leads to guide channel 31 which, like insertion channel 26, extends axially, in substantially parallel relation to axis A—A. Guide channel 31 leads to second lateral channel (or "catch portion") 32, which is bounded by forward stop surface 32a, a rearward stop surface 32b and an axial surface 32c. Both surfaces 32a and 32b may be disposed in perpendicular relation to axis A—A, but surface 32b is preferably disposed at a slightly oblique angle relative to axis A—A and extends from guide channel 31 towards axial surface 32c with a slight incline towards proximal end 22b.

Figure 5:
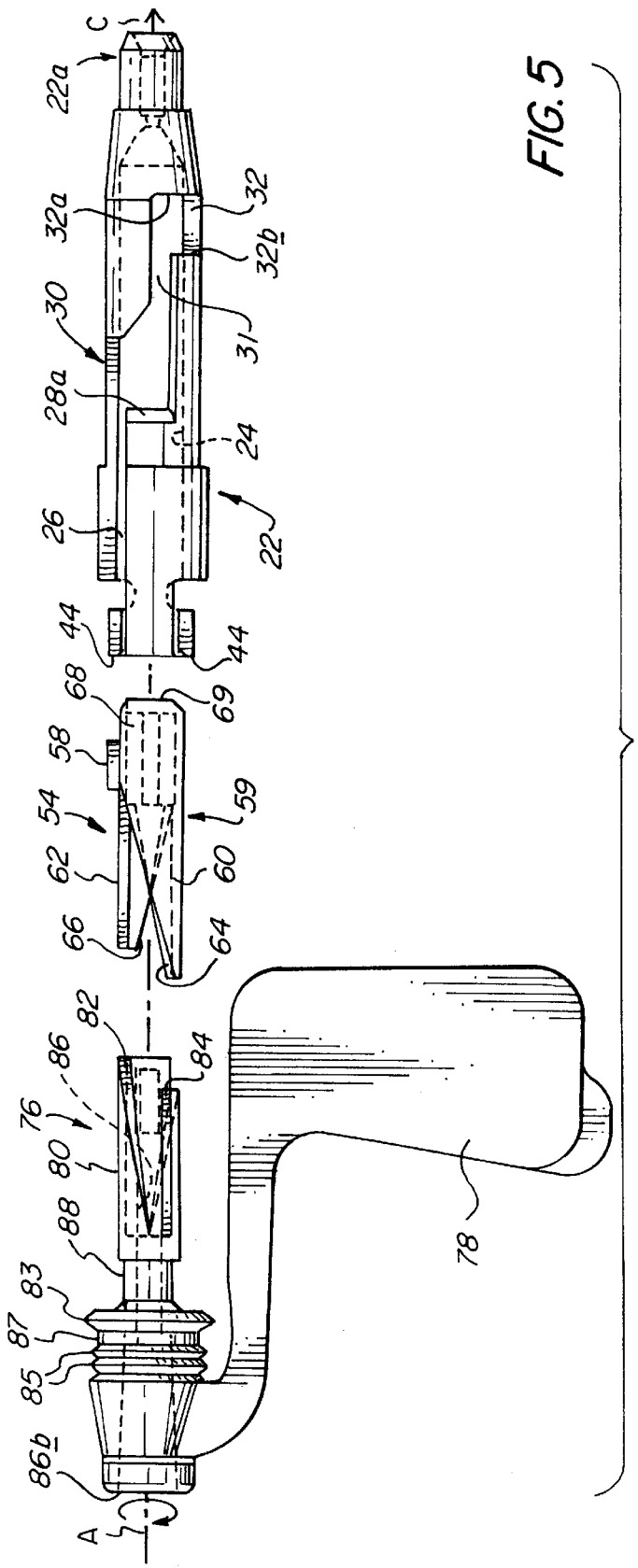
FIG. 5 depicts the driver, shuttle member and body member of FIG. 2 in axial alignment with one another.

FIG. 5 illustrates numerous structural details of driver 76 and shuttle 54 as well as hollow body 22. Driver 76 comprises a generally cylindrical driver body 76a that has a driver passageway 86 extending therethrough from a proximal aperture 86b. Third wing 78 extends from driver body 76a to provide a deployment haft that is designed to be manipulated by the user. As indicated above, proximal aperture 86b is dimensioned and configured to couple with a conventional fluid flow connector. The opposite end of driver body 76a defines a cam member 80 on which cam surfaces 82 and 84 are formed. In its central region, driver body 76a defines coupling features including rings 85, trough 87, ring 83 and retention groove 88 intended to facilitate the coupling of driver 76 with other structures in the apparatus, as will be described further below.

FIG. 5 also shows shuttle 54 disposed in spaced alignment with driver 76 along a common axis A—A. Shuttle 54 is generally cylindrically shaped and has a blunting member reception aperture 68 (shown in phantom) extending therethrough for coaxial reception of blunting member 70 (FIG. 2). Aperture 68 opens outwardly at one end of shuttle 54 to define a frusto-conical region 69. Region 69 serves the dual purpose of facilitating insertion of the blunting member into aperture 68 and of presenting a rim for the reception of an annular bead of adhesive to bond the outer surface of the blunting member to shuttle 54. Blunting member 70 is mounted in and is disposed generally coaxially with shuttle 54 and preferably extends both forwardly and rearwardly of shuttle 54. The portion of blunting member 70 that extends forwardly of shuttle 54 is preferably dimensioned and configured to be telescopically received within the interior of needle 12 without obstructing the needle component passageway to fluid flow therethrough. The rearwardly extending portion of blunting member 70 may be received in the aperture in driver 76 when driver 76 engages shuttle 54, as described below.

Shuttle 54 comprises the blunting component hub for blunting member 70 and together these structures comprise the blunting component of the apparatus. A blunting component passageway extends through shuttle 54 and blunting member 70.

Shuttle 54 defines a cam follower portion 59 that includes first and second tines 60 and 62 having first and second following surfaces 64 and 66, respectively. Each of first and second following surfaces 64 and 66 preferably defines a surface which is oriented perpendicularly to axis A—A and defines a helix about axis A—A. Two tines are not essential: a single tine and following surface may be employed.

First and second following surfaces 64 and 66 are designed for sliding engagement with complementary cam surfaces 82 and 84 on cam member 80. When shuttle 54 engages cam member 80 and is constrained for motion along axis A—A, the complementary cam and following surfaces convert rotational motion of driver 76 about axis A—A relative to both the needle component and to the blunting member into translational motion of shuttle 54 along axis A—A. Such constraint is achieved by disposing shuttle 54 and cam member 80 in body 22 (FIG. 2), with spline 58 in cam channel 30. FIG. 5 depicts driver 76 and shuttle 54 in axial alignment with hollow body 22. Upon assembly, shuttle 54 and the blunting member 70 (FIG. 2) attached thereto are inserted into cavity 24 with spline 58 disposed in cam channel 30. Then, cam member 80 is inserted into cavity 24 such that first and second cam surfaces 82 and 84, respectively, mate with companion first and second following surfaces 64 and 66 of cam follower portion 59. Then, lock tabs 44 snap into retention groove 88, thus rotatably coupling driver 76 to body 22 so that cam member 80 can rotate within body 22.

Figure 6B:
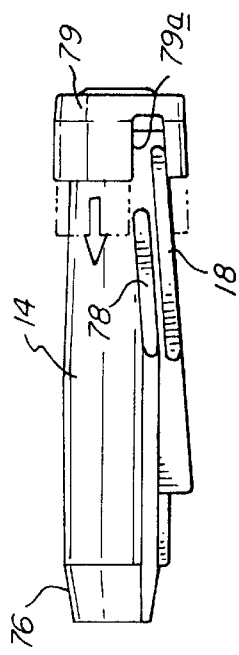
FIG. 6B is a cross-sectional elevation side view of the body member and winged sheath shown in FIG. 6A.
Figure 6C:
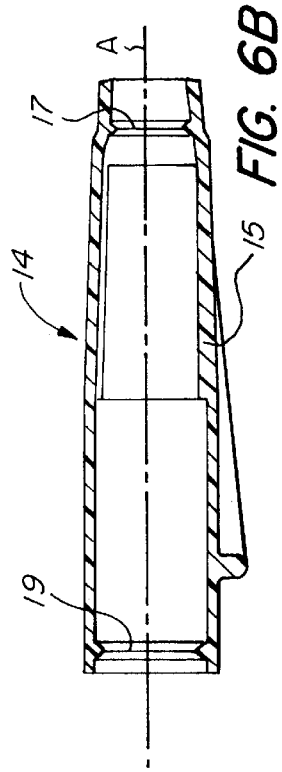
FIG. 6C is a side elevation view of the winged sheath and driver of the needle apparatus of FIG. 1 in combination with an alternative locking means.
Figures 6A, 7A:
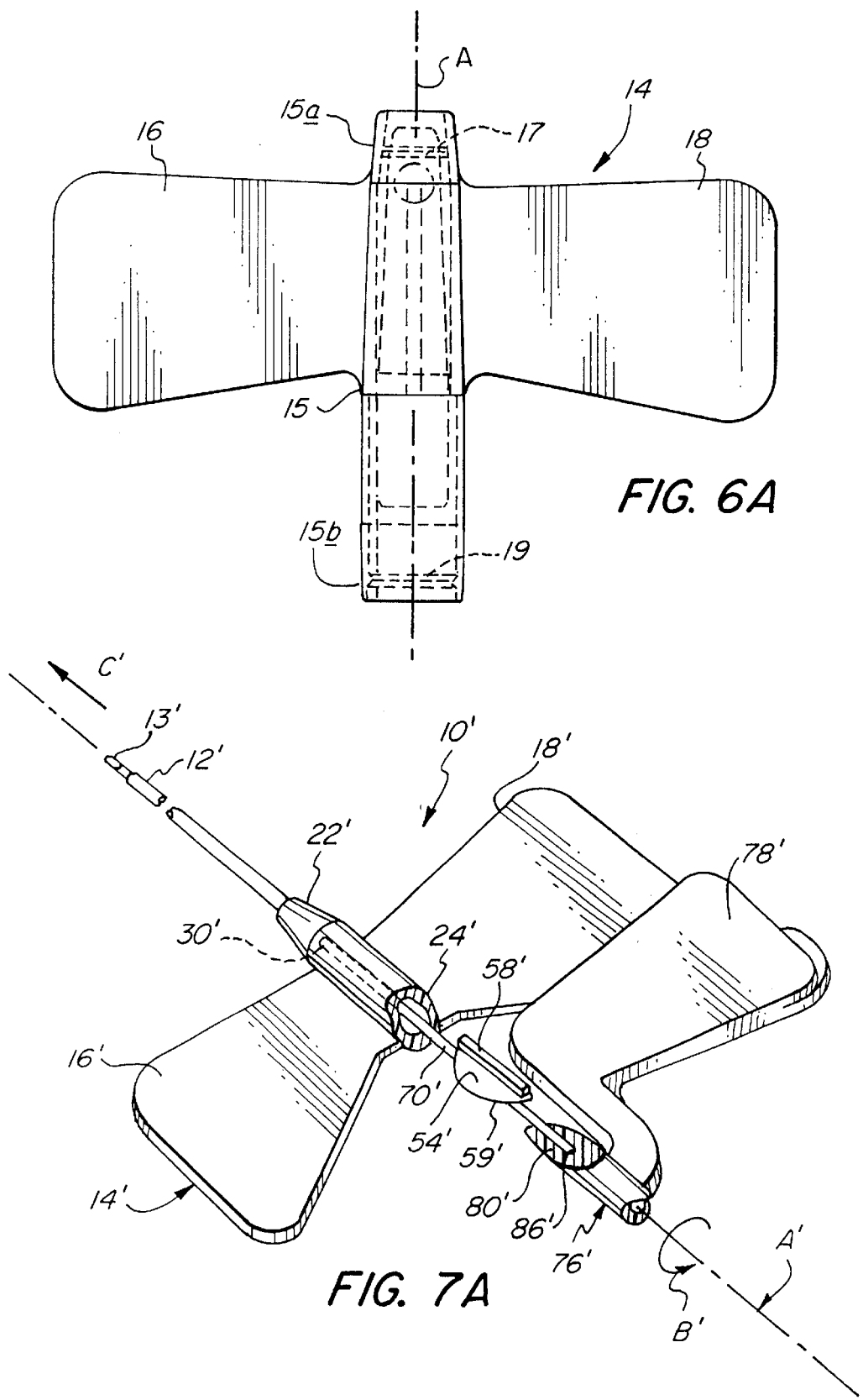
FIG. 6A is a top plan view of the body member and winged sheath of the apparatus shown in FIGS. 1 and 3.
FIG. 7A is a partially exploded, perspective view of another embodiment of an apparatus in accordance with the present invention.

Winged body 14 is illustrated in FIGS. 6A and 6B. Winged body 14 comprises a generally cylindrical central member 15 having a distal end 15a and a proximal end 15b. Central member 15 defines distal locking ring 17 in its distal end 15a and a proximal locking ring 19 in its proximal end 15b. Central member 15 of body 14 is dimensioned and configured to fully receive hollow body 22 with proximal end 15b and proximal locking ring 19 extending beyond the proximal end 15b of hollow body 22. When cam member 80 of driver 76 is then inserted into hollow body 22, ring 19 can engage annular trough 87 between rings 83 and 85 of driver 76, and sealingly engage driver 76, e.g., at ring 83, while permitting rotational movement between them. Winged body 14 will be sealingly secured to hollow body 22, e.g., by a sealant/adhesive so the combination of winged body 14, hollow body 22 and needle 12 may be viewed as together constituting the needle component of the illustrated embodiment.

The assembly of apparatus 10 (FIG. 1) may proceed as follows. With reference now to FIG. 2, the end 12a of needle 12 is secured in the distal end 22a of hollow body 22. Needle 12 is inserted into cavity 24 at needle insertion funnel 40 until a terminal end of needle 12 is seated within first cylindrical region 38 and abuts the hollow circular junction wall. The frusto-conical shape of insertion funnel 40 facilitates alignment of needle 12 into cylindrical region 38, as disclosed in commonly assigned patent application Ser. No. 08/772,002 of M. J. Burzynski et al for "Self-Blunting Needle Medical Devices and Methods of Manufacture Thereof". Needle 12 is fixed to hollow body 22 with a generally annular film of adhesive disposed between the outer surface of needle 12 and insertion funnel 40. Similarly, blunting member 70 is inserted into shuttle 54 via region 69 and is secured therein. Blunting member 70 is then inserted into body 22. As mentioned above, blunting member insertion funnel 34 facilitates insertion of blunting member 70 into cylindrical region 36. Since the diameter of region 36 is preferably substantially equal to or smaller than the inner diameter of needle 12, funnel 34 and cylindrical region 36 cooperate to facilitate initial insertion of blunting member 70 within the interior of needle 12. The telescopically disposed combination of needle 12 and blunting member 70 comprises the cannula component of the apparatus. When blunting member 70 is received within the needle 12, fluid flowing through the blunting component passageway will also flow through the needle component passageway. Thus, the blunting component does not obstruct fluid flow through the needle component of the apparatus. In other embodiments, the blunting component need not define a passageway extending therethrough; it may be sufficient to provide an aperture to allow fluid to enter the needle component passageway and for the structures of the blunting component, e.g., the blunting member and shuttle, to be physically configured to allow fluid to flow around them within the needle component passageway. In still other embodiments, the blunting component may both be dimensioned and configured to define a blunting component passageway and to permit fluid to flow around it within the needle component passageway. All such configurations serve to permit the flow of fluid through the needle and to permit the movement of the blunting component within the needle component without obstructing or significantly affecting fluid flow therethrough.

As blunting member 70 enters needle 12, shuttle 54 enters cavity 24 with spline 58 in cam channel 30. Then, as indicated above, cam member 80 of driver 76 is inserted into cavity 24 of hollow body 22 so that cam surfaces 82 and 84 engage first and second surfaces 64 and 66 of shuttle 54. Once driver 76 has been fully received within hollow body 22, tabs 44 cooperate with a circumferential retention groove 88 on driver 76 to rotatably couple driver 76 with hollow body 22. The assembly of driver 76, hollow body 22 and needle 12 may then be inserted into the proximal end 114 of winged body 14 with needle 22 passing through the internal passage therein so that rings 17 and 19 of winged body 14 engage hollow body 22 and driver 76, respectively.

As described above, spline 58 is initially disposed in insertion channel 26 and it has been shown that apparatus 10 is configured to permit rotational movement of driver 76 relative to the needle component and to shuttle 54 and blunting member 70, which are movable relative to the needle component. When driver 76 is rotated by the manipulation of third wing 78, the complementary cam surface/ following surface engagement of cam member 80 and shuttle 54 will tend to advance shuttle 54 within body 22. The user thus advances the blunting component in an axial direction by applying a rotational force to the apparatus. Such advancing movement will be constrained by the spline-and-cam channel engagement of the blunting component and the needle component of the apparatus, i.e., of shuttle 54 and hollow body 22. The resulting motion of spline 58 will be in an axial direction along insertion channel 26, then in a lateral or rotational direction into and through first lateral channel 28, guided by slide surface 28*b*.

Thereafter, further rotation of cam member 80 in body 22 advances shuttle 54 towards the distal end 22*a* of body 22 along axis A—A within guide channel 31. Blunting member 70 is dimensioned so that as shuttle 54 advances within hollow body 22 towards distal end 22*a*, the blunt end of blunting member 70 does not protrude beyond the puncture tip at puncture tip 13 of needle 12 at least until spline 58 enters guide channel 31 (FIGS. 4A and 4B). Further rotation of driver 76 will cause spline 58 to move forward axially in guide channel 31 and then laterally or rotationally into second lateral channel 32. It should be noted that first tine 60 of shuttle 54 (and first following surface 64 thereon) is longer than second tine 62 and second following surface 66. Similarly, first cam surface 82 of cam member 80 is longer than second cam surface 84. Cam surface 82 and following surface 64 are dimensioned and configured to generate axial and rotational movement of shuttle 54 as driver 76 rotates in the direction of arrow B about axis A—A. By the time spline 58 is aligned with second lateral channel 32, the shorter of the complementary surfaces (second cam surface 84 and second following surface 66) will no longer be in contact with one another and further motion of shuttle 54 will be due to the engagement of first cam surface 82 and first following surface 64. However, once first cam surface 82 causes shuttle 54 to rotate so that spline 58 enters second lateral channel 32, reverse rotation of driver 76 will disengage the complementary cam/following surfaces, leaving spline 58 positioned within second lateral channel (or "catch portion") 32 between forward stop surface 32*a* and rearward stop surface 32*b*. Thus, upon complete extension of blunting member 70, third wing 78 will become rotatable independently of shuttle 54. Further, shuttle 54 will be incapable of further movement along axis A—A either in the direction of, or opposite to that of, arrow C. Backward axial movement of shuttle 54, which may be imposed if the blunted apparatus accidentally contacts a user's skin, will then cause spline 58 to engage surface 32*b*. If spline 58 slides along surface 32*b*, surface 32*b* will guide spline 58 away from guide channel 31, towards axial surface 32*c*. The blunting component is configured so that even if spline 58 retreats as far as surfaces 32*b* and 32*c* will allow, it will still extend beyond the tip of the needle and blunt the apparatus. Accordingly, once spline 58 has entered second lateral channel 32, it will be "locked" therein against axial movement within body 22 until and unless shuttle 54 is rotated within hollow body 22 to re-align spline 58 with guide channel 31.

In alternative embodiments, the spline may be mounted on the body member and the channel may be formed in the shuttle. Thus, in a spline and channel configuration, either one of the shuttle and the body member may comprise the spline and the other may comprise the channel. Alternative locking means, such as a groove and lock tab arrangement comparable to tabs 44 and retention groove 88 may be employed, if desired. Optionally, the apparatus may comprise unlocking means for moving the spline from the locked position back into alignment with guide channel 31 and, optionally, for retracting the blunting member to return the apparatus to the insertion configuration. In various embodiments, the needle could be mounted on the shuttle and extend into the blunting member, which would be mounted on the hollow body. In such case, the initial insertion configuration would require that the shuttle start at the distal end of the hollow body, and the action of the driver would be to retract the shuttle towards the proximal end to withdraw the puncture tip behind the blunt end of the blunting member. The complementary cam/following surfaces and the orientation of the locking means would have to be reversed relative to apparatus 10.

Those of ordinary skill in the art will appreciate that a wide variety of other cam member/cam follower configurations could also be employed to translate the rotation of driver 76 into axial movement of shuttle 54. For example, while cam member 80 and follower portion 59 provide two pairs of complementary cam/following surfaces, other embodiments can function similarly as long as there is at least one pair of complementary surfaces.

Referring again to FIGS. 1 and 2, the central portion 15 of winged body 14 serves the advantageous purpose of ensuring that no air seeps into the fluid which flows through apparatus 10 during fluid transfer. Such air seepage is undesirable, for example, because it causes foaming of a fluid sample as the fluid is drawn into the fluid reservoir. In particular, central member 15 is disposed around winged body 14 in a manner which prevents air from being drawn into an associated fluid reservoir through the space between the various adjoining components (e.g., driver 76 and hollow body 22) during blood collection operations. Air seepage is inhibited at one end of apparatus 10 by the engagement of rings 85 of winged driver 76 and the corresponding ring 19 on winged body 14 (FIGS. 6A and 6B), which form an air-tight seal between them. Similarly, ring 83 bears against central member 15 to form a seal therebetween. Air seepage is prevented at the other end of apparatus 10 by cooperation between ring 17 (FIGS. 6A and 6B) on winged body 14 and an annular wall 37 (FIG. 4A) on hollow body 22, which form an air-tight seal therebetween as well. Component sealing can optionally be enhanced by applying viscous lubricant/sealant to the components of apparatus 10. In particular, the lubricant/sealant can, inter alia, be applied to an annular trough 87 of driver 76.

When apparatus 10 is fully assembled (as seen in FIGS. 1 and 3), driver 76 is rotatably coupled to the needle component and the passageway 86 extending through it communicates with the needle component passageway. Thus, driver 76 and the needle component are disposed in a tandem configuration, in which fluid enters one of these two and can then flow through the next. The blunting component is disposed substantially entirely within the needle component because the blunting member hub, i.e., shuttle 54 and the forward portion of blunting member 70, are disposed within the needle cannula 12 and the needle hub, i.e., hollow body 22. Fluid can flow through the apparatus in either direction, i.e., into proximal aperture 86*b* (FIG. 5), through the fluid flow passageway of the device (i.e., through driver 76, through the blunting component and through the needle component) and out needle 12 or in the opposite direction, into needle 12, through the apparatus and out proximal aperture 86*b*. In addition, the needle component and blunting component will be movable relative to each other, from an insertion configuration in which the puncture tip at the puncture tip of needle 12 extends beyond the blunt end of the blunting member to a blunted configuration in which blunting member 70 protrudes past the puncture tip to blunt the apparatus. Typically, such movement will entail the sliding advancement of blunting member 70 through needle 12. Optionally, blunting member 70 may be configured to leave an annular space between it and the interior surface of needle 12, and apparatus 10 may include a viscous, optionally silicone (polymeric organo-silicon)-based, lubricant/sealant disposed at least between the inner surface of needle 12 and the outer surface of blunting member 70. A bead of such lubricant/sealant may be deposited around blunting member 70 so that it is disposed at insertion funnel 34 of cavity 24 in body 22, where it serves as a small reservoir to coat and seal blunting member 70 as it moves into needle 12.

As indicated above, one end of collection tube 72 is preferably connected to driver 76 such that tube 72 is in fluid communication with passageway 86 (see FIG. 5) at proximal aperture 86b. Since tube 72 (FIG. 3) terminates at luer adapter 74, fluid communication between tube 72 and one of a wide variety of well-known fluid reservoirs having a standard luer adapter fitting thereon is possible. Alternatively, luer adapter 74 could be replaced by another fitting to accommodate other fluid reservoirs, or passageway 86 (FIG. 5) could be directly connected to another type of fluid flow apparatus.

In apparatus 10, first and second wings 16 and 18 effectively act as stops which limit the rotation of third wing 78, which serves as an actuator by which the user can conveniently rotate driver 76. Thus, third wing 78 is capable of rotational movement about axis A—A between a first position, wherein third wing 78 is adjacent first wing 16 (see FIGS. 1 and 3), and a second position wherein third wing 78 is adjacent second wing 18. During one method of usage, it is customary to fold first and second wings 16 and 18 toward one another just prior to and during venipuncture. If this procedure is utilized, third wing 78 will naturally be urged into a position which is midway between the above-described first and second positions. In order to accommodate this customary practice, cam member 80 and cam follower portion 59 of shuttle 54 are preferably designed such that rotation of third wing 78 from the first position to the above-described midway position does not impart substantial axial motion to shuttle 54 along axis A—A, i.e., such movement is not sufficient to move the apparatus from the insertion configuration to the blunted configuration. Thus, during venipuncture, blunting member 70 will not extend forwardly of puncture tip 13 of needle 12. Wings 16 and 18 and even third wing 78 therefore provide a non-deploying haft, meaning that even when they are displaced (i.e., in the case of wings 16 and 18, folded together) from their "neutral" or flat configuration to an upright configuration, they do not deploy the blunting member or blunt the needle. Stated in the converse, in this embodiment the deployment means effects deployment of the blunting member independently of the use of the haft. After insertion of needle 12, however, first and second wings 16 and 18 may be relaxed to their original position and third wing 78 will be rotated from the midway position to the above-described second position. During this rotation of third wing 78, shuttle 54 is urged from its retracted positioned (the insertion configuration) to its extended position (the blunted configuration) to thereby blunt needle 12. Alternatively, the user may grasp third wing 78 for use as a haft to effect insertion of needle 12. In such case, third wing 78 will be disposed in an upright position, midway between wings 16 and 18, which lie flat and act as guides against the patient's skin. Even in such use, third wing 78 is held in the midway position and does not blunt the needle until it is rotated to its second position. After deployment of the blunting member, third wing 78 can be freely rotated about axis A—A either in the direction of, or opposite to, arrow B without imparting movement to shuttle 54. Thus, first and second wings 16 and 18, together with third wing 78, may be securely taped to a patient during fluid delivery and/or withdrawal operations in the usual manner. Since blunting member 70 is locked in a forwardly extending position due to the cooperation of spline 58 and second lateral channel 32, apparatus 10 may be subsequently untaped, removed from the patient and discarded without exposing a healthcare worker to the sharpened puncture tip 13 of needle 12.

The various components of apparatus 10 may be fabricated from a wide variety of materials. For example, needle 12 and blunting member 70 may be formed of stainless steel or some other corrosion-resistant metal. Further, hollow body 22, shuttle 54 and winged driver 76 are preferably formed of one of the many durable, semi-rigid, and moldable plastic materials. Winged body 14, by contrast, is preferably formed from a thermoplastic elastomeric material. Using such a relatively pliant material to form winged body 14 serves the dual purpose of allowing wings 16 and 18 to be freely flexed and of ensuring that central member 15 of winged body 14 provides an air-tight seal around hollow body 22. Any one of a number of well-known adhesives may be used to affix needle 12 to hollow body 22 and to affix blunting member 70 to shuttle 54.

In alternative embodiments, needle apparatuses in accordance with the present invention may comprise various types of locking mechanisms. For example, the locking means for an apparatus in accordance with the present invention may comprise a sliding locking member such as a chuck 79 mounted thereon. FIG. 6C shows a needle apparatus comprising a winged body 14 having a first wing (not shown) and a second wing 18 and a driver 76 rotatably coupled thereto. Driver 76 carries a third wing 78 that provides an actuator to be manipulated by the user to deploy the blunting member as described above, except that in the embodiment of FIG. 6C, driver 76 does not disengage from the blunting member during reverse rotation. However, winged body 14 carries on it a slidably disposed chuck 79 which, in the forward position shown in FIG. 6C, remains clear of third wing 78. When third wing 78 is moved against wing 18 as shown in FIG. 6C to deploy the blunting member of the device, the user may slide chuck 79 rearward so that third wing 78 is disposed within gap 79a of chuck 79, as suggested in dotted outline. So positioned, chuck 79 will inhibit the reverse rotation of third wing 78 and help prevent inadvertent re-sharpening of the needle. Alternatively, wing 78 may carry a slidable clip member (not shown) that can be moved into place to engage wing 18 when wing 78 is disposed against it as shown in FIG. 6C.

As alluded to above, the locking spline and cam channel engagement between the blunting component and the needle component shown in FIG. 3A and FIG. 5 can be employed advantageously in apparatuses other than flow-through, winged needle apparatuses, regardless of whether the blunting component obstructs fluid flow when deployed or whether the blunting component comprises an oblique motion deployment means. For example, the spline and cam channel engagement could be incorporated into a self-blunting syringe in place of a tooth-and-groove arrangement shown in U.S. Pat. No. 4,828,547 (discussed above) or a detent-and-shoulder or a snap ridge-and-groove arrangement as shown for a syringe plunger in U.S. Pat. No. 5,527,284 to Ohnemus et al, dated Jun. 18, 1996. For example, syringe 110 shown in FIG. 6D comprises a syringe barrel 120 which is intended to hold an injectable fluid to be administered through the movement of plunger head 130 therethrough. A plunger arm 126 is connected to plunger head 130 and terminates in a thumb rest (not shown) that is accessible from outside barrel 120 and upon which the user presses the thumb while holding the fingers against a finger rest (not shown) on-barrel 120. A needle 112 is mounted in a hub portion that comprises needle mount 116, the barrel 120 on which it is mounted and the hollow body 122 secured therein. A blunting member 170 is disposed movably within the needle component and extends telescopically within syringe 110. Blunting member 170 comprises a shuttle 154. Hollow body 122 is dimensioned and configured to receive shuttle 154 therein and to engage shuttle 154 in a spline and cam channel configuration. Accordingly, shuttle 154 comprises a spline 58 and hollow body 122 comprises a cam channel configured substantially like cam channel 30 of hollow body 22 (FIGS. 4A and 4B) except that the cam channel of hollow body 122 comprises a slide surface 228 leading to the second lateral channel of the cam channel. The blunting component of syringe 110 comprises blunting member 170, shuttle 154 and the driving means movable relative thereto, i.e., a plunger comprising plunger head 130 and plunger arm 126. The driving means engages the needle component at the interior of barrel 120. When initially assembled, syringe 112 is filled with injectable fluid and the apparatus is disposed in the insertion configuration, i.e., blunting member 170 is retracted within needle 112 by positioning shuttle 154 near the proximal end 122*b* of hollow body 122. The user manipulates the driving means, i.e., depresses plunger arm 126, to make plunger head 130 bear against blunting member 170 to move it towards its extended position, i.e., into the blunting configuration, and to advance spline 58 through the cam channel of hollow body 122. As this occurs, the plunger forces the injectable fluid in barrel 120 through needle 112. When the injection is complete, spline 58 is disposed within the second lateral channel of hollow body 122, thus locking the syringe 110 in the blunted configuration. Shuttle 154 and blunting member 170 are configured to permit fluid flow around and/or through them, through hollow body 122 and needle 112, respectively. Optionally, the portion of blunting member 170 that resides in barrel 120 may be perforated to allow the injectable fluid in barrel 120 to enter the hollow interior of blunting member 170. Syringe 110 thus provides an embodiment of the present invention in which the spline and cam channel locking means is utilized with a blunting component that comprises a hydraulic driver instead of a non-hydraulic driver. Optionally, blunting member 170 may be configured so that it does not enter needle 112 until the intended dose of fluid in barrel 120 has entered the proximal end 112*a* of needle 112. In such case, the blunting component 170 need not necessarily comprise a non-obstructive blunting component.

Figure 7H:
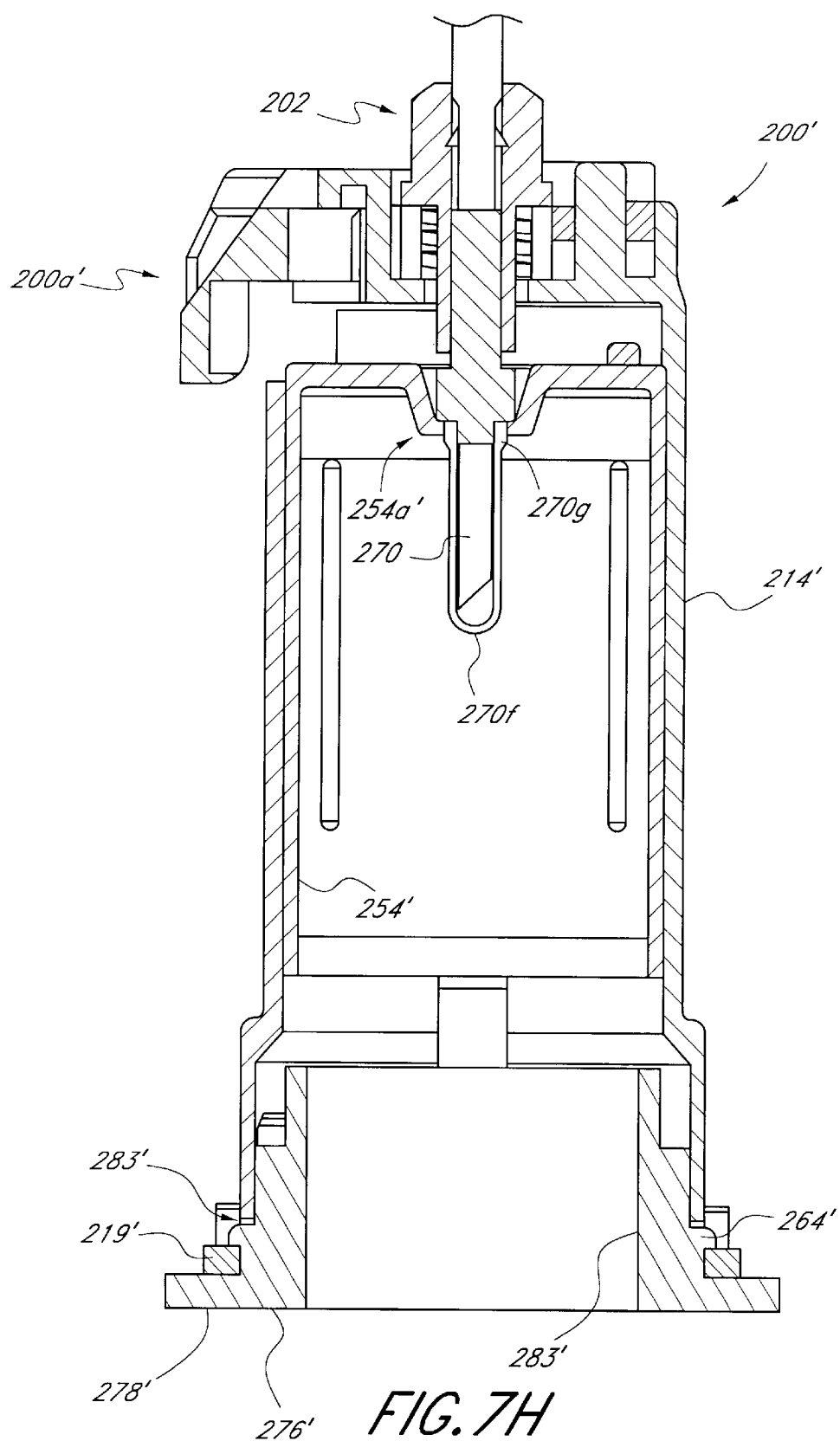
FIG. 7H is a cross-sectional view of a particular embodiment of a blood collection needle as generally represented by FIGS. 7B–7G.
Figure 12A:
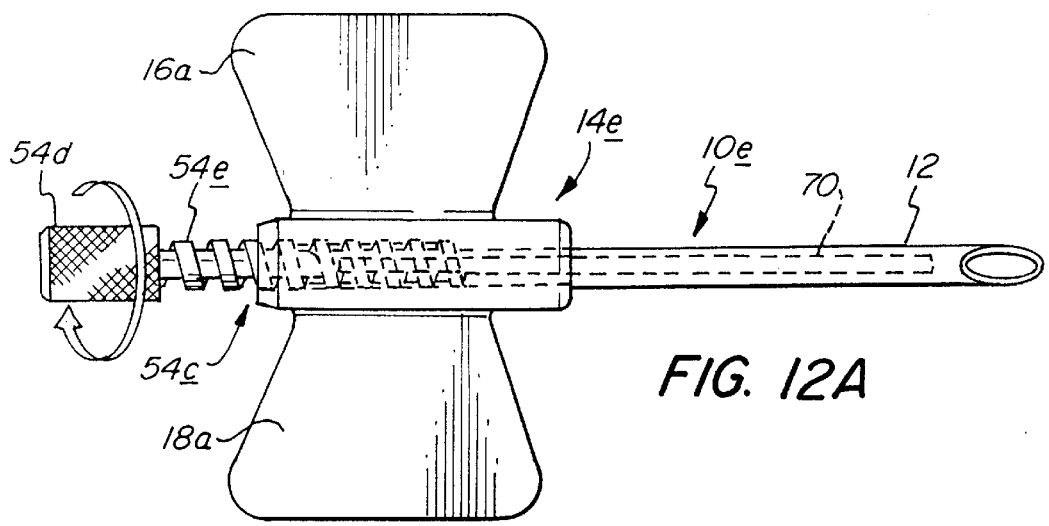
FIG. 12A is a plan view of a screw thread embodiment of a needle apparatus.

An alternative preferred embodiment of the present invention is depicted in FIG. 7. While the alternative embodiment of FIG. 7 contains a cam/cam follower configuration which is distinctly different from that of the above-discussed preferred embodiment, the embodiment of FIG. 7 also bears a number of similarities with the above-discussed referenced embodiment. For example, apparatus 10' comprises a winged body 14', a blunting member shuttle 54', a blunting member 70', a winged driver 76' and a needle 12'. In this embodiment, winged body 22' integrates the salient features of winged body 14 and hollow body 22 of the previously described embodiment. Thus, winged body 22' defines a generally cylindrical hollow cavity 24' extending axially along an axis A'—A' and has first and second wings 16' and 18' that extend from opposite sides thereof. Needle 12' is fixed to the distal end 22*a'* of winged body 22' such that needle 12' extends forwardly of the distal end of winged body 22', which serves as the needle hub. The needle component of this embodiment is therefore constituted by winged body 22' and needle 12'. Winged body 22' forms a cavity 24' that defines a cam channel 30' which extends therein parallel to axis A'—A'. Blunting member shuttle 54' is generally cylindrically shaped and includes an elongated spline 58' which is complementary in cross section to cam channel 30' for slidable engagement therewith. Shuttle 54' is disposed about a tubular blunting member 70' such that, when shuttle 54' is received within cavity 24', blunting member 70' extends along axis A'—A' and is telescopically received within needle 12'. Shuttle 54' may move between a retracted position, wherein blunting member 70' does not extend forwardly of puncture tip 13' of needle 12' and an extended position, wherein blunting member 70' does extend forwardly of the puncture tip 13' of needle 12'. Also, shuttle 54' includes a cam follower portion 59' with a planar elliptical surface disposed on the rearward face of shuttle 54'. Blunting member 70' and shuttle 54' constitute the blunting component of this apparatus.

As with the above-described preferred embodiment, the embodiment of FIG. 7 further comprises driver 76' having a third wing 78' and a generally cylindrical cam member 80'. Cam member 80' is sized and shaped to be received within cavity 24' and includes a passageway 86' extending therethrough for receiving the rear end of blunting member 70'. Cam member 80' also includes a substantially elliptical camming surface which faces the cam follower portion 59' of shuttle 54'. As shown in FIG. 7, driver 76' is capable of rotation about axis A'—A' in the direction of arrow B' between a first position, wherein third wing 78' lies immediately adjacent second wing 18' and a second position, wherein third wing 78' lies immediately adjacent first wing 16'. Driver 76' may be sealingly but rotatably connected to body 22' by complementary rings and grooves (not shown) as described above for apparatus 10' in tandem relation to the needle component. Those of ordinary skill will readily appreciate that upon rotation of third wing 78' from the first position to the second position, the rotational movement thereof will impart linear movement to blunting member shuttle 54' along axis A'—A' in the direction of arrow C'. Naturally, such movement of shuttle 54' will also blunt needle 12' by urging blunting member 70' forwardly of puncture tip 13' of needle 12'. Thereafter, third wing 78' is freely rotatable about axis A'—A' between the first and second positions without imparting further movement to shuttle 54'.

The embodiment of FIG. 7 may also include a variety of features previously described with respect to the above-discussed preferred embodiment. These features may include a blunting member locking mechanism, means for retaining blunting member shuttle 54' and cam member 80' within hollow cavity 24', and the presence of a viscous lubricant/sealant between needle 12' and blunting member 70'. Additionally, the various apertures may include any one or more of the contoured features of hollow body 22' which facilitate assembly of apparatus 10' as described above. It should be noted that the rotatable driver and shuttle member may be configured to rotate about the longitudinal axis of the apparatus in either direction, with wing 78' moving from right to left (as sensed and shown in FIG. 7) or from left to right to deploy the blunting member. Finally, the various components of apparatus 10' may be fabricated from the various materials discussed above with respect to the components of apparatus 10'.

In apparatuses 10 and 10', the illustrated blunting components are dimensioned and configured to have a flow aperture therethrough. Such a configuration of the blunting component, however, is not a necessary limitation for such embodiments of the invention; the present invention would encompass a similar embodiment in which, e.g., the blunting member had a solid cross section but was dimensioned and configured to permit fluid flow around it within the needle component. For example, even if the blunting member and shuttle are solid and configured for a friction fit within the needle and hub, they may make only partial contact with the interior of the needle component by virtue of, e.g., generally longitudinal (axial) flutes or grooves along its surface, to permit fluid flow around the blunting component rather than through it. In any case, the blunting component of the present invention is configured so that it does not obstruct the flow of fluid through the flow passageway of the apparatus in either the insertion configuration or the blunted configuration.

Another aspect of apparatuses 10 and 10' is that the winged bodies, which are designed to provide a convenient handling aid to facilitate venipuncture, effectively comprise parts of the needle components of those apparatuses. In alternative embodiments, the handling wings or other feature intended to facilitate handling may comprise part of the blunting or the optional driving means.

As previously indicated, various aspects of the present invention are not limited to wing set embodiments. For example, FIGS. 7B through 7H illustrate a blood collection needle 200 that embodies various aspects of the present invention. Blood collection needle 200 comprises a self-blunting needle assembly 202, a holder 214, an inner sleeve 254 and a driver 276. The self-blunting needle assembly 202 provides a cannula component comprising a needle cannula and a blunting member disposed telescopically one within the other with the two being movable between a sharpened configuration and a blunted configuration. In the sharpened configuration, the sharp tip of the needle cannula extends beyond the blunt tip of the blunting member; in the blunted configuration, the blunt tip of the blunting member extends beyond the tip of the needle cannula and thus prevents the needle from puncturing tissue under typical hand pressure. Needle assembly 202 is shown in greater detail in FIGS. 7C and 7D, which shows that needle cannula 212 is mounted in a hub body 222 to provide a needle component for the device. The blunting member 270 is hollow, defines a blunt tip 270a, and is disposed telescopically within the needle cannula 212. Blunting member 270 carries thereon a nut 270b that defines annular grooves 270c and 270d. The hub body 222 defines detents 222a, 222b on flex arms 222e and 222f that cooperate with annular grooves 270c and 270d to define preferred rest positions for the blunting member relative to the needle component corresponding to the blunted configuration and the sharpened configuration. Hub body 222 defines a threaded portion 222c by which the needle component is mounted on holder 214 in a conventional manner and an open internal bore 222d which at least partially includes a mounting passage 222d within which needle 212 is mounted. Preferably, but optionally, passage 222d defines at least one, preferably two, divergent openings at its ends that are dimensioned and configured in a funnel-like manner to facilitate the mounting of needle cannula 212 in hub 222 and/or the insertion of blunting member 270 into needle cannula 212. Optionally, passage 222d and the divergent opening(s) thereto may be formed in a ferrule 222e that is mounted in an open internal bore formed in hub 222, as shown. Alternatively, passage 222d and its divergent opening(s) may be formed integrally with hub 222. Blunting member 270 terminates at a sharpened tip 270e that is covered by a resilient, puncturable and self-sealing boot 270f. As is well-known in the art, boot 270f prevents the leakage of blood from needle assembly 202 when needle cannula 212 is inserted into a patient's vein and before a blood sample vial is secured thereto. Boot 270f forms an anchor region 270g that has a greater outer diameter than the rest of boot 270f because it rests on an anchor ferrule 270h on nut 270b. Part of nut 270b forms an annular cup 270j into which anchor ferrule 270h and boot 270f extend. Anchor region 270g grips ferrule 270h in a friction fit to inhibit removal of boot 270f therefrom, and cup 270j may be crimped onto boot 270f for added stability. Tip 270e permits blunting member 270 to puncture boot 270f and the seal on a conventional sample vial as in a manner known in the art.

Referring again to FIG. 7B, self-blunting needle assembly 202 is mounted on holder 214 which serves as a haft because it is customary in the field of phlebotomy to manipulate the needle cannula by grasping the holder. Self-blunting needle assembly 202 is mounted at the distal or forward end 214a of holder 214, i.e., at the end which, in use, is generally directed away from the user. Holder 214 defines an interior region dimensioned and configured to receive therein the inner sleeve 254 into which the sharpened end of the blunting member extends. Inner sleeve 254 is dimensioned and configured to receive therein a conventional blood collection vial or "sample vial" which typically comprises a stoppered evacuated sample tube.

Inner sleeve 254 is dimensioned and configured to be slidably received within holder 214. Inner sleeve 254 defines one or more tabs 258 that protrude from the exterior surface of inner sleeve 254. The interior of holder 214 is dimensioned and configured to slidably receive tabs 258 and to limit the movement of inner sleeve 254 within holder 214 to axial relative motion and to prevent rotation of inner sleeve 254 within holder 214. To accommodate tabs 258 in this way, holder 214 may define wings 214c.

At the rearward end 214b, holder 214 defines an internal engagement lip 219 for engaging driver 276 as described below.

Driver 276 is now described with reference to FIG. 7E. Driver 276 comprises a generally annular body 283 and a radially-extending flange 278 which the user can employ as an actuator to rotate the driver 276. Body 283 is dimensioned and configured to be received within the rearward end of holder 214 and to receive therein a sample vial. The exterior surface of body 283 defines one or more cam channels 283a. Body 283 and tabs 258 (FIG. 7B) are dimensioned and configured so that body 283 can be received between tabs 258 and lugs 264 can be slidably disposed within cam channels 283a.

To assemble the device, needle assembly 202 is mounted in holder 214. Inner sleeve 254 is then inserted into the interior of holder 214 and inner sleeve 254 engages the blunting component 270. The body 283 of driver 276 is then inserted into the rearward end 214b of holder 214 and is received between tabs 258 with lugs 264 disposed within cam channels 283a. Body 283 is inserted into holder 214 until engagement lip 219 engages groove 287 to rotatably retain driver 276 therein. Then, by grasping holder 214 in one hand and flange 278 of driver 276 in the other hand, the user can rotate driver 276 and, due to the cam action of tabs 258 in cam grooves 283a, can move the needle assembly 202 from a sharpened configuration shown in FIG. 7F to the blunted configuration shown in FIG. 7G by advancing and retracting inner sleeve 254 and the blunting member secured thereto within holder 214. The illustrated blood collection needle thus embodies an oblique motion deployment means and a driver that rotatably engages the haft member.

A particular embodiment of a blood collection needle as described above is illustrated in FIG. 7H. Blood collection needle 200' comprises a holder 214' within which the self-blunting needle assembly 202 is mounted. Holder 214' optionally comprises a quick-release mechanism 200a' for the convenient disposal of needle assembly 202 when blood sampling is complete. Alternatively, needle assembly 202 can be screwed or otherwise secured into a conventional holder fitting. Mechanism 200a' is not part of the present invention per se, so it will not be described herein. However, reference may be made to U.S. Pat. No. 5,755,673, dated May 26, 1998, which patent is incorporated herein by reference for background purposes with respect to the detailed description of the quick-release mechanism described therein. The needle cannula of needle assembly 202 and holder 214' are co-axially aligned.

Holder 214' defines a substantially cylindrical interior cavity within which a generally cylindrical inner sleeve 254' is disposed. The forward end 254a' of inner sleeve 254' is dimensioned and configured for a friction fit with cup 270j of nut 270b and is thus coupled with blunting member 270 so that axial movement of inner sleeve 254' within holder 214' is effective to move needle assembly 202 between the sharpened and blunted configurations.

A driver 276' comprises a generally annular body 283' and a radially-extending flange 278', and it engages a retaining lip 219' formed on holder 214'. When driver 276' thus rotatably engages the rearward end of holder 214', lugs 264' carried on driver 276' engage cam grooves 283a' in holder 214'. Thus, the user can move needle assembly 202 between the sharpened configuration and the blunted configuration by rotating driver 276' about the axis of the needle to move inner sleeve 254'. Cylindrical body 283' and inner sleeve 254' are dimensioned and configured to receive a standard blood collection vial therein.

In use, the user grasps holder 214' to insert the sharpened needle cannula into the patient's vein before inserting the sample vial into the holder 214'. At any convenient juncture thereafter, the user may rotate driver 276' to move the needle assembly 202 to the blunted configuration. The user inserts a standard blood collection vial through the hollow interior of body 283' and inner sleeve 254' so that the stopper on the vial presses against boot 270f. The pressure on boot 270f causes the sharp tip on blunting member 270 to penetrate the boot 270f and the stopper on the vial, which is typically evacuated. Blood is then drawn through the needle assembly 202 into the vial. When the vial is full or a suitable volume of blood has been drawn, the vial may be withdrawn from holder 214'. Boot 270f will return to its initial configuration, effectively sealing the blunting member 270 and thus preventing unwanted flow of blood through the needle assembly until a subsequent sample vial is inserted into holder 214' or until the blood collection needle 200' is withdrawn from the patient's vein.

Apparatus 10a of FIG. 8 exemplifies another embodiment of the present invention. Apparatus 10a comprises a needle component comprising needle 12 that is secured to a hub portion comprising a winged body 14a. Winged body 14a comprises a central member 15' that serves the same purpose as hollow body 22 of apparatus 10 (FIG. 2). In contrast to the previously described embodiments, it is the needle component of apparatus 10a that is configured to be coupled with a fluid flow device. Thus, central member 15' defines a passage therethrough that communicates and flows into the hollow interior of needle 12. In addition, central member 15' comprises a needle component end 15a that is dimensioned and configured to be coupled to a flow device such as a tube, luer, or the like.

The blunting component of apparatus 10a comprises a blunting member 70 (shown in dotted outline) which is slidably disposed within the needle 12. In FIG. 8, the apparatus 10a is shown in the insertion configuration, i.e., blunting member 70 is withdrawn into entry needle 12 such that the puncture tip is fully exposed. Blunting member 70 comprises a shuttle portion (not shown) that is disposed within central member 15'. The blunting component is dimensioned and configured to permit fluid flow between needle component end 15a and the puncture tip of needle 12 at all times. The shuttle portion of the blunting component comprises a lug 92 that protrudes through an access aperture in the form of a lug slot 94 formed in central member 15'. As used herein, the term "access aperture" refers to a slot or other opening in the needle component or the blunting component that exposes a portion of the other component therein without permitting biologic fluid to flow through the aperture. For example, the outer surface of the blunting component seals off the lug slot 94 by engaging the inner surface of central member 15' even though lug 92 protrudes therethrough. Referring now to FIG. 8A, slot 94 comprises an axially-oriented travel portion 94a and a catch portion 94b. Travel portion 94a extends for an axial distance sufficient to allow spline 58 to move from its retracted position to its extended position, i.e., from the insertion configuration to the blunted configuration. At the apex of such motion, shuttle 58 engages diversion surface 94c, which is disposed in oblique relation to travel portion 94a, and which causes the shuttle (not shown) to rotate within central member 15' so that spline 58 enters catch portion 94b. Catch portion 94b is bounded in part by a stop surface 94d which will prevent a direct reverse axial force from moving spline 58 (and therefore the blunting component of the apparatus) back into the retracted (i.e., insertion) position. Accordingly, spline 58 and slot 94 provide an alternative embodiment of locking means in accordance with the present invention.

Referring again to FIG. 8, apparatus 10a comprises deployment means comprising a tension line 90, which may comprise a nylon filament, metal wire, or other flexible high tensile strength fiber. Tension line 90 is anchored at one end on wing 16 at an anchor 90a which may comprise a spot of adhesive or any other suitable device for anchoring the end of line 90 on wing 16. The other end of line 90 is anchored at a corresponding anchor 90c on wing 18, and the middle of line 90 is secured to spline 58. Anchors 90a and 90c are situated forward of the initial position of lug 92. Winged body 14a is configured so that wings 16 and 18 fold along hinge lines disposed on the bottom of winged body 14a while spline 58 extends beyond the blunt end of the blunting member at the top of winged body 14a. Wings 16 and 18 are initially constrained in a folded, upright manipulation position that facilitates handling the needle cannula venipuncture, and line 90 is configured so that as long as the wings are in this folded, initial configuration, spline 58 can remain in the retracted position. When wings 16 and 18 are folded down after venipuncture by the user's application of generally lateral forces thereon, the separation of the anchors draws line 90 taut, pulling spline 58 forward into the extended position, as shown in FIG. 8B. Thus, folding down the wings moves the apparatus from the insertion configuration to the blunted configuration.

As indicated above, a deployment means is an optional feature used only in certain embodiments of the present invention; in other embodiments, an apparatus according to the present invention may simply comprise the needle component and the blunting component. Such an embodiment is represented by apparatus 10b shown in FIG. 9. Apparatus 10b comprises a needle 12 connected to a winged body 14b which together comprise a needle component which is the outer component of apparatus 10b. Blunting member 70 and the shuttle (not shown) on which it is mounted therein comprise the inner component. In this embodiment, the outer component, i.e., the needle component, not only defines a first aperture, i.e., the opening of the needle cannula at the sharp puncture tip, but it also provides a second aperture 186b to which other fluid flow devices can be attached. Accordingly, the outer (needle) component encloses the inner (blunting) component, and the apparatus establishes a fluid flow passageway from the first aperture to the second aperture. The outer component further defines an opening or access aperture through which the user can manipulate the inner component. Specifically, winged body 14b defines an axially-oriented slot 94'. The shuttle therein carries a lug 92 that protrudes through the access aperture provided by slot 94' and which can be manipulated by the user, e.g., pushed with a finger in a forward axial direction to advance the blunting component of the device, i.e., to apply force in the direction in which the needle was inserted. Preferably, the blunting component is rotatable therein and apparatus 10b comprises locking means comprising a catch portion of slot 94' similar to that shown in FIG. 8A. When it is desired to lock the blunting component in the extended position, lug 92 is rotated so that it engages the catch portion of the slot. The blunting component will then resist backwards motion until the user once again aligns lug 92 with the main portion of the slot. In an alternative embodiment, the lug itself is rotatable. Such a lug, e.g., lug 92a (FIG. 9A), can be rotated when in the extended position to engage catch portion 94b of slot 94a.

According to still other embodiments of this invention, the deployment means may comprise a pliant or deformable portion of the outer component, and the inner component may be configured to move therein in response to deformation of the outer component. For example, apparatus 10c (FIG. 10) comprises a blunting component that is entirely disposed within the needle component when the apparatus is in the insertion configuration. In apparatus 10c, winged member 14c comprises a manually deformable central member 15''' in which needle 12 is mounted and which comprises an end 15c that provides a proximal aperture to which a fluid flow device may be connected. The shuttle portion 54a and the interior of central body member 15''' are configured so that after venipuncture, the user may apply lateral or radial force on the apparatus by squeezing body member 15''' of winged body 14c and may thus urge shuttle portion 54a and the blunting member 70 thereon forward, i.e., away from end 15c, to project the blunt end of blunting member 70 beyond the puncture tip of needle 12. For example, shuttle portion 54a may have a tapered configuration that narrows towards end 15c. Shuttle portion 54a and blunting member 70 are configured to permit fluid flow through the needle component at all times. For example, they may define a blunting component passageway therethrough.

Another apparatus comprising a deployment means comprising a deformable outer component in accordance with the present invention is shown in FIG. 11. Apparatus 10d comprises a needle 12 mounted in a hub comprising winged body 14d. Blunting member 70 is mounted in a blunting component hub that provides a piston 54b. Rearward of piston 54b, winged body 14d defines a pliant portion 15d that defines a fluid reservoir for a working fluid 15e sealed therein between piston 54b and the slidable sealed engagement region 15f of blunting member 70 and winged body 14d. Since blunting member 70 never leaves engagement region 15f and piston 54b forms a seal with winged body 14d, working fluid 15e resides only outside blunting member 70 and is thus isolated from the flow passageway of the apparatus. The flow passageway of the apparatus extends from the proximal aperture into the blunting member, through piston 54b and to the distal aperture of needle 12. After venipuncture, the user can squeeze pliant portion 15d to cause working fluid 15e to advance piston 54b (and therefore the blunting member) forward without significant hydraulic effect on biologic fluid in the flow passageway of the apparatus. Internal stop lugs 15g prevent piston 54b from moving so far forward that blunting member 70 is withdrawn from engagement region 15f. It may be noted that the wings may be folded for venipuncture without compressing pliant portion 15d.

Yet another embodiment of the invention is illustrated in FIG. 12. In this Figure, apparatus 10e comprises a needle component comprising needle 12 and a needle hub comprising winged body 14e. The blunting component comprises blunting member 70 and blunting component hub 54c, which protrudes from the end of winged body 14e. Hub 54c comprises a collet portion 54d that is dimensioned and configured for convenient manipulation by the user. Hub 54c is also dimensioned and configured to define the proximal aperture of the apparatus 10e, for convenient coupling with a fluid flow device such as a tube 72 (FIG. 1). Hub 54c also comprises a threaded portion 54e that engages complementary threads (not numbered) within winged body 14e. In use, apparatus 10e is initially in the insertion configuration, as shown in FIG. 12, and the user handles wings 16a and 18a for venipuncture. Then, the user can manipulate the collet portion 54d to move the apparatus to the blunted configuration, in which the blunt end of blunting member 70 protrudes beyond the puncture tip of needle 12. To accomplish this, the user rolls collet portion 54d between the thumb and index finger, thus screwing the blunting component into winged body 14e and advancing blunting member 70 into needle 12 until the apparatus is in the blunting configuration with the blunt end of blunting member 70 extending beyond the puncture tip at the puncture tip of needle 12. This rolling motion allows the user to deploy the blunting member without applying a pushing force directly in an axial direction, i.e., in the direction in which the needle was inserted. Thus, the threaded engagement of the blunting component and the needle component provides a deployment means for the apparatus. Further, since direct rearward axial pressure on the extended blunting member will not cause the device to change from the blunted configuration back to the insertion configuration, this threaded embodiment can be described as providing a locking means that is integral with the deployment means.

Figure 12B:
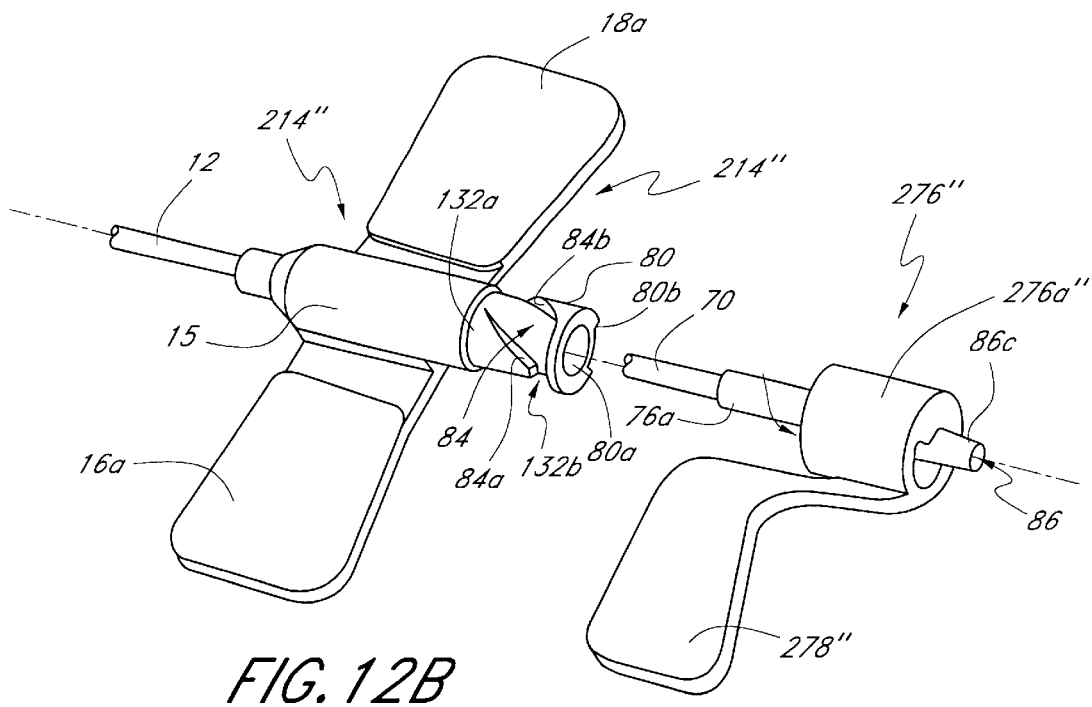
FIG. 12B is an exploded perspective view of a needle apparatus having a rotatable drive member and a detent and catch slot locking means.
Figure 12C:
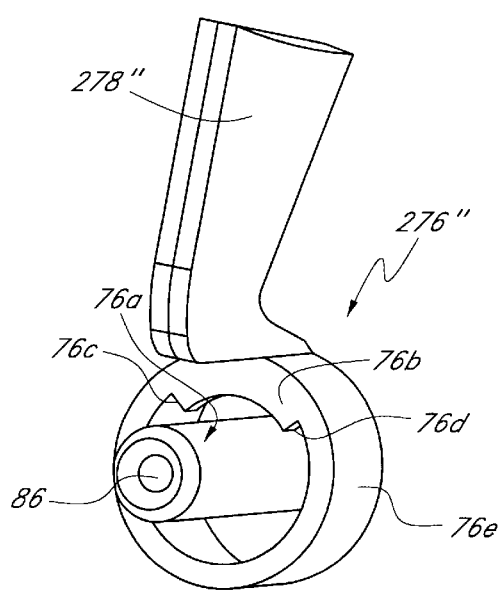
FIG. 12C is a different perspective view of the drive member of FIG. 12B.
Figure 12D:
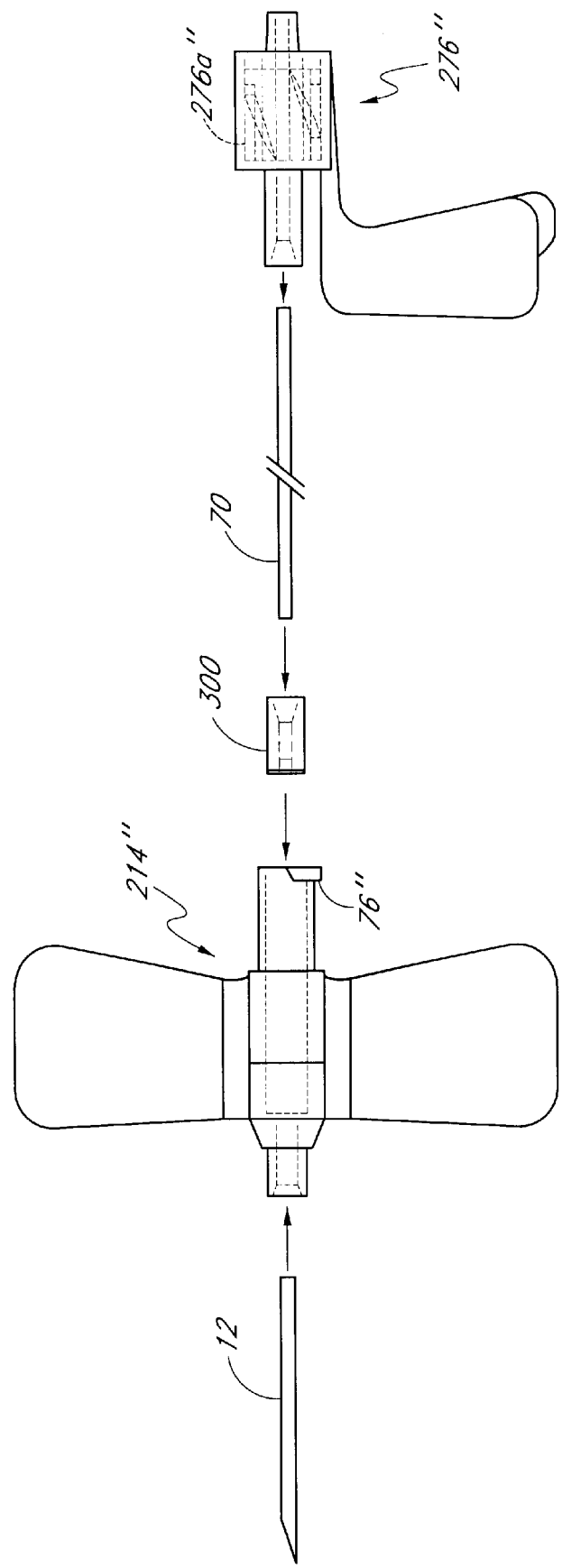
FIG. 12D is a schematic plan view of an alternative embodiment of the apparatus illustrated in FIGS. 12B and 12C.

Another embodiment of a wing set comprising an oblique motion deployment means in accordance with the present invention will be understood with respect to FIGS. 12B and 12C. FIG. 12B provides an exploded view of the winged needle apparatus which comprises two moving parts, a needle component comprising a needle cannula 12 mounted in a winged body 214". As seen in FIG. 12B, driver 276" comprises a driver body 276a" and a third wing 278" for convenient manipulation of the driver by the user. Driver 276" comprises at the rearward portion thereof a fitting 86c that defines an aperture 86 that communicates with the hollow interior bore of blunting member 70. Fitting 86c has a slightly tapered configuration for convenient insertion into the end of a convention fluid flow device or tube through which biologic fluids may be delivered to or withdrawn from the winged needle apparatus.

Winged body 214" defines at its rearward end a cam extension 80 that defines an internal bore 80a that communicates with the internal bore of cannula 12. In addition, bore 80a is dimensioned and configured to receive blunting member 70 and collet 76a in which the blunting member is mounted therein. Cam extension 80 defines a generally spiral slot 84 bounded by cam surfaces 84a and 84b. It also defines a circumferential catch slot 132a that communicates with slot 84 that is disposed radially about the axis of winged body 214".

FIG. 12C depicts the driver 276" with the blunting member removed to simplify the Figure. It can be seen that collet 76a defines a passageway therethrough with a beveled opening to facilitate the insertion of blunting member 70 therein. In the perspective of FIG. 12C, it can also be seen that driver 276" defines an inwardly-extending tooth 76b. Tooth 76b is configured to be received within slot 84 on the cam extension 80 of winged body 214, preferably with end surfaces 76c and 76d positioned sufficiently close to cam surfaces 84a and 84b so that driver 276" does not move axially relative to winged body 214" without rotation about the needle axis. In addition, tooth 76b has an axial width that allows it to rotate circumferentially into catch slot 132a.

Cam extension 80 defines an entry notch 80b and an entry slot 132b that communicates with cam slot 84. To assemble the device, tooth 76b is aligned with entry notch 80b and blunting member 70 is inserted into bore 80a until tooth 76b enters notch 80b. Then, the driver 276" is rotated so that tooth 76b travels through entry slot 80c and into cam slot 84. In this initial position, wing 78 is positioned close to wing 16a and the wing set is in a sharpened configuration, in which the blunt tip of blunting member 70 is withdrawn into the interior of needle cannula 12. Preferably, the winged needle apparatus is configured so that third wing 78 can be rotated to the 90-degree position between the haft wings 16a and 18a without blunting the needle cannula. The user can then insert the needle cannula into a vein in the usual manner, e.g., by bending wings 16a, 18a and 78 together as a haft to manipulate the needle for insertion into the patient's vein. Once the needle is in its proper position, the wings are released and allowed to lie flat and can be taped to the patient's skin. Wing 78 is then rotated further and the forward motion of tooth 76b in cam slot 84 moves the blunting member forward so that the blunt tip of the blunting member protrudes beyond the tip of the needle cannula. The needle device is thus moved from the sharpened configuration to the blunted configuration. (Reverse rotation of wing 78 can move the device back to the sharpened configuration by moving blunting member 70 rearward.) Upon full rotation, tooth 76b is aligned with catch slot 132a. The user may then counter-rotate wing 78 into contact with wing 76a while keeping driver 276" in the forward position, which action moves tooth 76b into catch slot 132a and away from cam slot 84. In this position, the blunting component is constrained against axial motion (i.e., is locked) relative to the needle member due to the configuration of catch slot 132a. The user may then tape the wing set to the patient's skin, securing wing 78 in the forward position, thus assuring that the device remains in the blunted configuration.

It will be understood that a tooth and cam slot engagement between the blunting member and needle member as shown in FIG. 12B may provide that the tooth be formed on the needle member and the cam slot on the blunting member. Such an embodiment is indicated in the exploded view of FIG. 12D, in which tooth 76" is carried on winged body 214" and driver 276" forms the entry slot, cam slot and locking slot on the interior surface of body 276a" as suggested in dotted outline.

Winged body 214" defines a bore extending therethrough and, at the forward end thereof, a beveled entrance to the bore configured similar to first end 22a (FIG. 2) of body 22 to facilitate the insertion of the rearward end of needle cannula 12 therein. A guide member 300 is inserted into the bore of winged body 214". Guide member 300 defines a passage therethrough, the forward end of which is aligned with, and is preferably not larger than, the bore through the needle cannula 12. The rear-ward end of the internal passage in guide member 300 diverges outwardly to form a funnel-like configuration so that when the blunting member is inserted into winged body 214", it can engage the divergent entrance of guide member 300 and be guided via the guide member passage into the needle bore. Guide member 300 also serves to provide a seal between the blunting member 70 and winged body 214". Optionally, guide member 300 can be formed integrally with winged body 214".

Optionally, locking means may be incorporated into any of the embodiments 10 of the present invention to hold the blunting component in the blunted configuration.

Figure 12E:
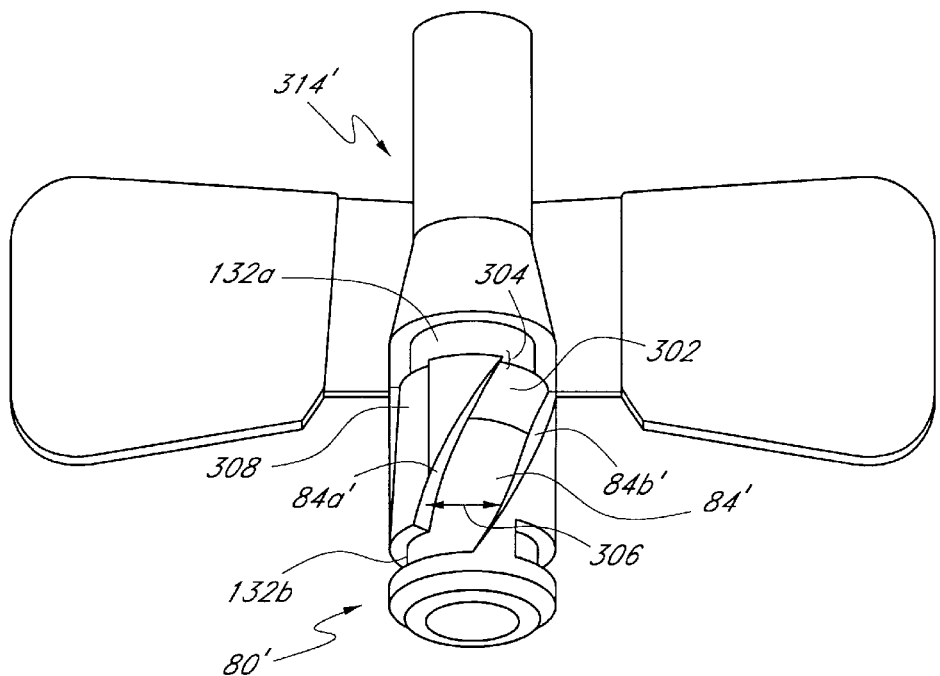
FIG. 12E is a perspective view of the winged body of a needle apparatus having ramp and detent locking means, a pinch region locking means and a reset ramp.
Figure 12F:
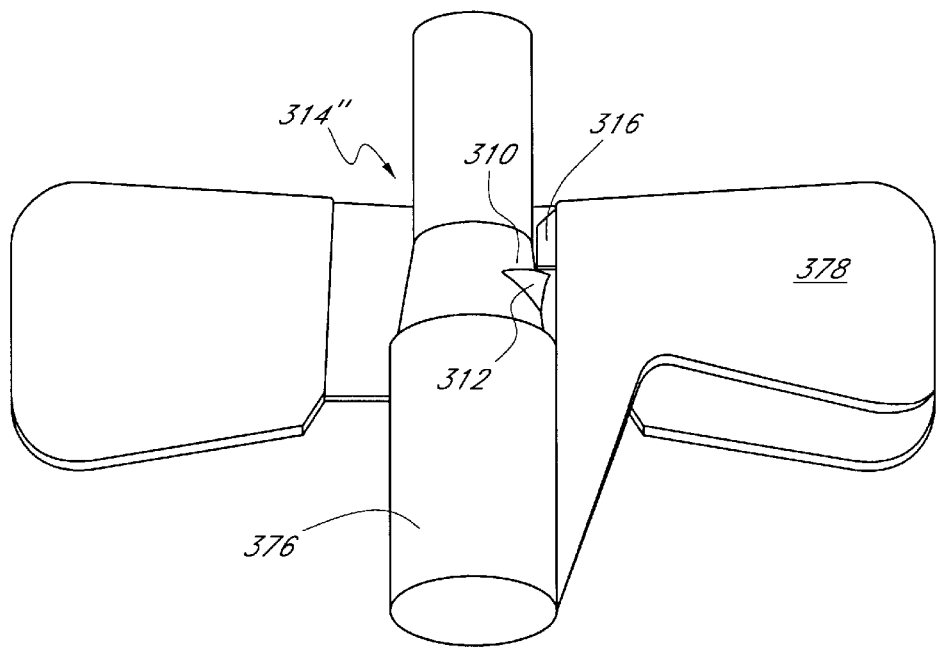
FIG. 12F is a view similar to FIG. 12E of an alternative ramp locking means.

In addition to the locking means previously described, FIGS. 12E and 12F illustrate further embodiments of locking means for use with wing set embodiments of the invention.

One such locking means embodiment comprising a tooth or detent on one member and a ramp on the other will be understood with reference to FIG. 12E, which shows a cam extension member 80' on winged body 314'. Cam extension 80' is configured generally like cam extension 80 of winged body 214 of FIG. 12B, with the following exceptions. At the forward end of axially-extending slot 84' (FIG. 12E) there is formed an axially-extending ramp 302 which is configured so that the distance from the axial center of winged body 314' to the surface of the ramp increases as sensed moving forward towards the tip of the needle. In this way, the detent on a driver (such as tooth 76b on driver 276", FIG. 12C) not only moves forward in slot 84' as the blunting member is advanced, it also rides up ramp 302 in the forward end of the slot towards catch slot 132a. The detent is biased so that when it advances past ramp 302 it will fall into catch slot 132a. Ramp 302 forms a shoulder that faces catch slot 132a so that once the detent has fallen into the catch slot 132a, rearward motion will cause it to bear against the shoulder of ramp 302 and the detent will prevent further rearward motion to the sharpened configuration. Ramp 302 thus provides a locking mechanism that tends to keep the blunting member in the forward, i.e., blunted, configuration, by inhibiting rearward movement of the blunting component. Optionally, the detent may be formed on a portion of the annular carrier member that is slotted on either side of the detent. The detent is thus mounted on a resilient leaf spring to facilitate its riding up ramp 302 and then falling in the catch slot 132a.

In addition to ramp 302, FIG. 12E illustrates another locking means which, although illustrated for use in conjunction with ramp 302, can be used independently thereof. This second locking means is provided by a pinch region 304 of slot 84' in which the width 306 of slot 84' gradually narrows. Accordingly, the tooth or detent of a driver member situated in slot 84' moves forward in slot 84' and reaches pinch region 304, the cam surfaces 84a' and 84b' bear against the lateral edges of the detent. Preferably, one or both of the tooth and the material forming cam surfaces 84a' and 84b' comprise resilient material so that the pressure of cam surfaces 84a' and 84b' against the sides of the detent does not prevent forward movement of the driver but rather causes elastic deformation of the tooth and/or the cam surfaces. Pinch region 304 opens abruptly to shoulders that straddle slot 84'. When the detent emerges from slot 84', one or both of the detent and the material forming cam surfaces 84a' and 84b' relaxes. As a result, the detent is not sized for entry into slot 84' from the forward end thereof. The narrowing of slot 84' in pinch region 304 and the resiliency of one or both of the detent and the cam surfaces that define the slot thus provide a locking means that inhibits the blunting member from moving rearward directly into slot 84' and toward the blunted configuration.

Optionally, a winged body comprising either or both of the locking means described above with reference to FIG. 12E may comprise a reset feature. In the illustrated embodiment, the reset feature is provided by return ramp 308. While the locking means, e.g., one or both of ramp 302 and pinch region 304, inhibits the detent on the driver from directly re-entering slot 84' once it has reached catch slot 132a, return ramp 308 is configured so that it is accessible to the detent from catch slot 132a. The user can then draw the driver backwards, moving the device from the blunted configuration to a sharpened configuration, until the detent falls from return ramp 308 into slot 132b. Return ramp 308 rises from catch slot 132a to form a shoulder that faces slot 132b so that the detent is inhibited from moving from slot 132b to catch slot 132a via return ramp 308. Once the detent has returned to slot 132b, the driver must be rotated once again to advance the detent into slot 84' and forward to the locking means.

Another ramp and detent embodiment of a locking means for use in a wing set embodiment is illustrated in FIG. 12F. In this Figure, winged body 314" carries a wedge 310 that defines a ramp 312 and a forward-facing shoulder. Third wing 378 on driver 376 carries a tooth or detent 316. The wedge 310 and detent 316 are dimensioned and configured so that when driver 376 is rotated to advance the blunting member thereon into the blunting configuration (as described, e.g., in regard to the device shown in FIG. 12B), detent 316 rides up on ram surface 312 and then falls in front of the shoulder formed by wedge 310. As a result, driver 376 is prevented from moving rearward should third wing 378 be counter-rotated.

Figure 13A:
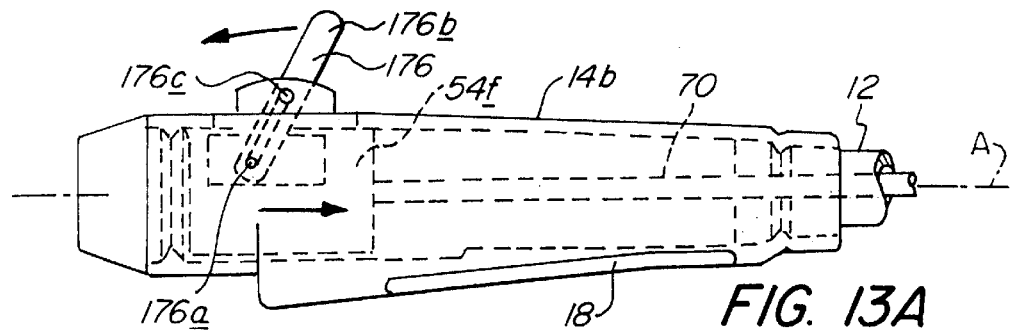
FIGS. 13A, 13B and 13C are elevation views of needle apparatuses comprising various reverse motion mechanisms.

A variety of other deployment means may be used to move the apparatus of this invention from the blunted configuration to the insertion configuration. For example, the deployment means may comprise a contrary motion linkage that moves the blunting member forward relative to the needle cannula in response to a rearward relative motion imposed on the deployment means by the user. The contrary motion linkage may take the form of a lever in which the first end of the lever is connected to one of the needle component and the blunting component, the fulcrum is connected to the other of these components and the user manipulates the second end of the lever. With the fulcrum so positioned, rearward motion of the user's second end of the lever will produce forward motion of the first end of the lever and of the component connected thereto. Such an embodiment is illustrated schematically in FIG. 13A, in which the drive member comprises a lever 176 having a first end 176a pivotably connected via an access aperture in winged body 14b to a shuttle 54f of a blunting component that comprises blunting member 70, and a second end 176b for manipulation by the user. The fulcrum 176c is mounted on winged body 14b between first end 176a and second end 176b, so that when the user pulls second end 176b rearward (to the left, as sensed in FIG. 13A), first end 176a moves generally forward, thus moving the apparatus from the insertion configuration to the blunted configuration.

Figure 13B:
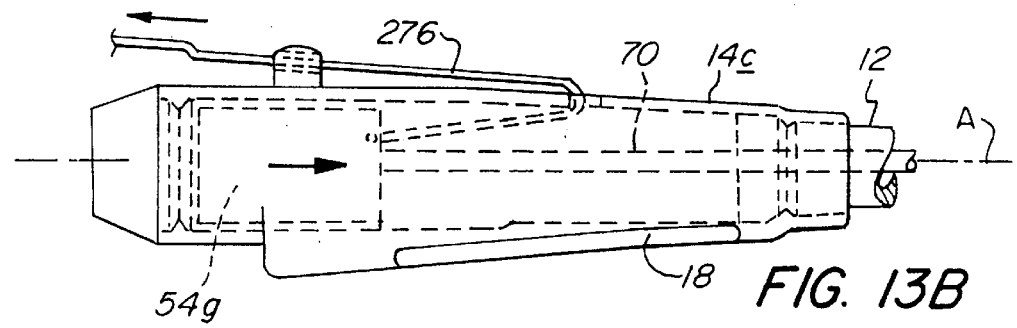

In an alternative contrary motion mechanism shown in FIG. 13B, the deployment means may comprise a tension line 276 that is attached to the blunting component shuttle 54g and which extends forwardly in a conduit within body 14c to an access aperture in the conduit, at which point it may be diverted backwards. When the user pulls on tension line 276 in a backwards direction, the line will pull the blunting component forwards. Optionally, tension line 276 may be connected to a partially coiled section of tubing coupled to the apparatus, and the blunting component may be deployed by straightening the partially coiled segment of tubing.

Figure 13C:
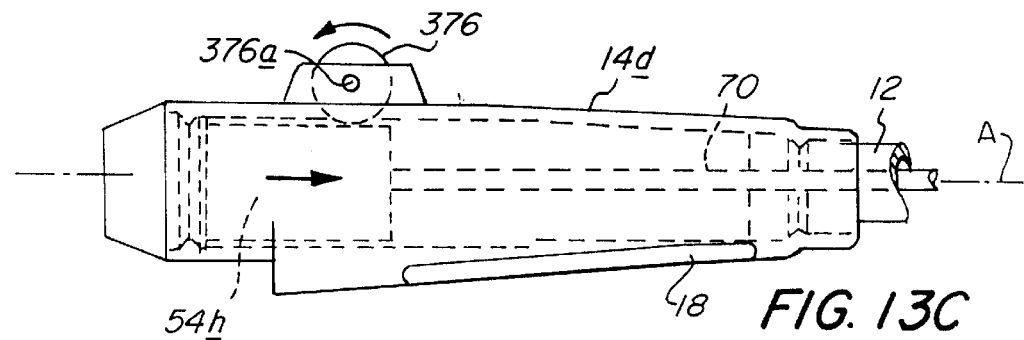

According to still another embodiment of the invention shown in FIG. 13C, the deployment means may comprise a drive member in the form of a roller 376 having an axle 376a mounted on one of the needle component and the blunting component, e.g., on the winged body 14d. Axle 376a, which defines the axis of rotation of roller 376, is disposed transversely, preferably at right angles, relative to the longitudinal axis of the needle cannula (not shown) in the apparatus. The cylindrical outer surface of roller 376 engages shuttle 54h via an access aperture in winged body 14d and when the user rolls the exposed portion of roller 376 in a backward direction, roller 376 can slide the blunting component in a forward direction. Optionally, a haft member corresponding to wings 18 can be mounted on axle 376a. In such an embodiment, the wings (not shown) may be displaceable so that they can be folded together (upward, as sensed in FIG. 13C) about a pivot point on the axis of axle 376a to facilitate insertion of the needle (not shown). Such displacement of the wings would not effect rotation of roller 376. To deploy the blunting component, the wings have to be turned about an axis that is substantially perpendicular to the longitudinal axis of the needle, to rotate the axle 376a on which roller 376 is provided.

Figure 14A:
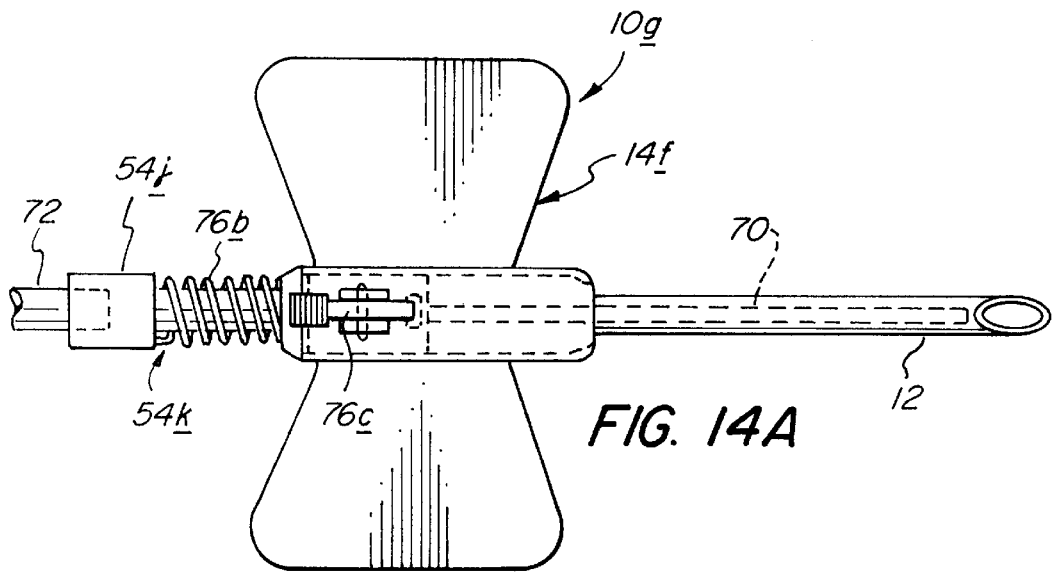
FIGS. 14A and 14B are plan and partially cross-sectional elevation views of a needle apparatus comprising a spring and release deployment mechanism.
Figure 14B:
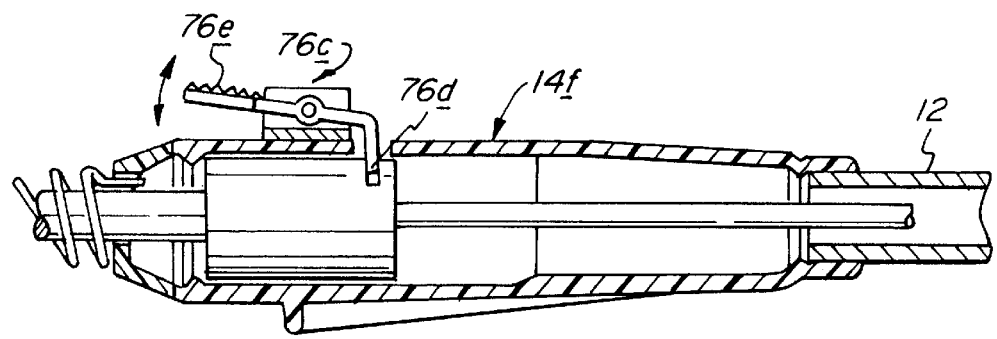

FIGS. 14A and 14B illustrate still another embodiment of the present invention, in which the deployment means comprises a stored energy device and a release mechanism. While such deployment means may be employed with any needle apparatus, it is illustrated in FIGS. 14A and 14B with respect to a apparatus 10g. Apparatus 10g comprises a needle 12 mounted in a winged body 14f that provides a hub for needle 12. The needle component, comprising winged body 14f and needle 12, is disposed in tandem relation with the blunting component, which comprises the blunting member 70 mounted on blunting component hub 54k. Hub 54k defines a proximal aperture (not numbered) to which a connector tube 72 may be secured. Blunting component hub 54k comprises a collet portion 54j to which one end of an extended spring 76b is secured. The other end of spring 76b is secured to the proximal surface 14g of winged body 14f. Accordingly, when apparatus 10g is disposed in the initial insertion configuration, spring 76b imposes a bias toward pulling collet portion 54j closer to winged body 14f, to advance the blunting member and moving apparatus 10g from the insertion configuration to the blunted configuration. To maintain apparatus 10g in the initial insertion configuration until venipuncture is accomplished, winged body 14f carries a release mechanism 76c. Release mechanism 76c comprises a detent member 76d that is pivotably mounted on winged body 14f, as best seen in FIG. 14B. Detent member 76d protrudes through an access aperture in winged body 14f and rests in a notch in blunting component hub 54k (not shown), where it prevents the blunting component from moving forward under the impetus of spring 76b. After venipuncture, the user depresses touch pad 76e, thus causing detent 76d to rise upward, withdrawing from the notch in the blunting component hub, as indicated by the movement arrows (not numbered). The blunting component is then free to move forwardly under the impetus of spring 76b.

The appended claims are intended to cover any and all of such modifications which fall within the spirit and scope of the invention and are not limited to the embodiments expressly described above.

What is claimed is:

1. A needle apparatus comprising:
   (a) a body member having a longitudinal axis, a distal end and a proximal end, and a longitudinal body passageway extending therethrough and connecting the distal end and the proximal end of the body member in fluid flow communication with each other;
   (b) a cannula component carried on the body member and disposed therein in fluid flow communication with the body passageway, the cannula component comprising a needle member and a blunting member, the needle member having a tissue puncture tip and a needle proximal end, and the blunting member having a blunting tip and a blunting member proximal end, the needle member and the blunting member being arranged with their respective tips facing in the same direction, and telescopically one within the other for relative axial movement of the needle member and the blunting member from (i) an insertion configuration of the cannula component, in which the tissue puncture tip extends beyond the blunting tip, to (ii) a blunted configuration of the cannula component, in which the blunting tip extends beyond the tissue puncture tip to blunt the same;
   (c) a shuttle member mounted for axial movement within the body passageway, the shuttle member (1) being dimensioned and configured to provide a first fluid flow passageway extending therethrough, and (2) engaging one of the blunting member and the needle member whereby axial movement of the shuttle member causes axial movement of the blunting member and needle member relative to each other to change the cannula component from its insertion configuration to its blunted configuration; and
   (d) a drive member in the body passageway which (1) extends beyond the proximal end of the body member, (2) is dimensioned and configured to leave the body passageway open to fluid flow between the distal and proximal ends of the body member, and (3) is operatively connected to the shuttle member, whereby manipulation of the drive member moves the shuttle member axially through the body passageway, thereby changing the cannula component from its insertion configuration to its blunted configuration, without significant hydraulic effect on fluid in the apparatus.

2. The apparatus of claim 1 wherein the drive member comprises a cam surface and the shuttle comprises a following surface, and further comprising:
   an actuator connected to the drive member and accessible for manipulation thereof from exteriorly of the body member, the drive member (1) being mounted for rotation within the body passageway, (2) being rotatable therein by manipulation of the actuator, and (3) operatively engaging the shuttle member, wherein manipulation of the actuator rotates the drive member to impose force on the following surface via the cam surface to move the shuttle member axially along the body passageway, thereby changing the cannula component from its insertion configuration to its blunted configuration.

3. The apparatus of claim 1 or claim 2 wherein the needle member is mounted on the body member and the blunting member is mounted on the shuttle member and is disposed telescopically within the needle member.

4. A needle apparatus comprising:
   (a) a body member having a longitudinal axis, a distal end and a proximal end, and a longitudinal body passageway extending therethrough and connecting the distal end and the proximal end of the body member in fluid flow communication with each other;
   (b) a cannula component carried on the body member and disposed therein in fluid flow communication with the body passageway, the cannula component comprising (1) a needle member having a tissue puncture tip and a needle proximal end, and (2) a blunting member having a blunting tip and a blunting member proximal end, the needle member and the blunting member being arranged with their respective tips facing the same direction and their respective proximal ends facing the proximal end of the body member, and with the blunting member disposed telescopically within the needle member for axial movement of the blunting member relative to the needle member from (i) an initial insertion configuration of the cannula component, in which the tissue puncture tip extends beyond the blunting tip, to (ii) a blunted configuration of the cannula component, in which the blunting tip extends beyond the tissue puncture tip to blunt the same;
   (c) a shuttle member mounted for axial movement within the body passageway, the shuttle member being dimensioned and configured to provide a first fluid flow passageway therethrough in fluid flow communication with the body passageway, and having the blunting member mounted thereon;
   (d) a drive member disposed within the body passageway and (1) being dimensioned and configured to provide a second fluid flow passageway extending therethrough and in fluid flow communication with the body passageway and (2) being operatively connected to the shuttle member such that rotation of the drive member moves the shuttle member and thereby the blunting member mounted thereon, axially along the body passageway in the direction towards the distal end of the body member for a distance sufficient to change the cannula component from its insertion configuration to its blunted configuration.

5. The apparatus of claim 4 wherein the drive member comprises a cam surface and the shuttle member comprises a complementary following surface, and further comprising:
   an actuator connected to the drive member and accessible for manipulation thereof from exteriorly of the body member, the drive member (1) being mounted for rotation within the body passageway, (2) being rotatable therein by manipulation of the actuator, and (3)

operatively engaging the shuttle member, wherein manipulation of the actuator rotates the drive member to impose force on the following surface via the cam surface to thereby move the shuttle member axially along the body passageway, thereby changing the cannula component from its insertion configuration to its blunted configuration.

6. The apparatus of any one of claims 1, 2, 4, or 5 further comprising locking means for inhibiting the apparatus from moving from the blunted configuration to the insertion configuration.

7. The apparatus of claim 6 wherein the locking means comprises a spline member and cam channel engagement of the shuttle member and the body member, the cam channel comprising an axially extending guide channel and a catch portion that connects with the guide channel at a lateral channel entryway, and the catch portion extending transversely of the guide channel and comprising a backward stop surface, wherein the spline member is dimensioned and configured to traverse the guide channel as the cannula component moves from the insertion configuration to the blunted configuration; and wherein the following surface of the shuttle member and the cam surface of the drive member are each dimensioned and configured so that rotation of the drive member in one direction advances the spline member along the guide channel and into the catch portion for engagement therewith, and rotation of the drive member in the opposite direction effectively disengages the cam follower and the cam surface, thereby locking the apparatus in the blunted configuration.

8. The apparatus of claim 6 wherein the locking means comprises (i) a detent on one of the shuttle member and the body member and (ii) an axially-extending ramp on the other, the ramp defining a shoulder, wherein the detent is positioned and configured to ride up the ramp as the shuttle member is advanced to be positioned to bear against the shoulder to inhibit rearward movement after the blunted configuration is attained.

9. The apparatus of claim 8 further comprising a return ramp for permitting the detent to move axially past the shoulder so that the apparatus can return to the insertion configuration.

10. The apparatus of claim 9 wherein the locking means comprises a detent and an axially-extending slot arrangement wherein the detent is positioned and configured to move axially in the slot as the shuttle member is advanced, and wherein the slot is configured to define a pinch region through which the detent passes, the pinch region being configured to inhibit entry of the detent into the slot once the blunted configuration is attained.

11. The apparatus of claim 10 further comprising a return ramp for permitting the detent to move axially past the shoulder so that the apparatus can return to the insertion configuration.

12. The apparatus of claim 2 or claim 5 wherein the blunting member comprises a tube having a tube bore extending therethrough.

13. The apparatus of any one of claims 1, 2, 4, or 5, wherein the drive member comprises a drive member hub and is mounted on the apparatus at the proximal end of the body member, and the shuttle member is interposed between the drive member and the distal end of the body member.

14. A needle apparatus having a fluid flow passageway and a proximal aperture for fluid flow therethrough, the apparatus comprising:

a needle component having a needle component passageway therethrough and comprising a hub portion and a needle cannula, the needle cannula having a longitudinal axis and being joined to, and extending from, the hub portion and having a proximal end and a puncture tip;

a blunting component comprising a blunting member and a blunting member hub, the blunting member having a proximal end and a blunt distal end and being joined to, and extending from, the blunting member hub and being dimensioned and configured to be received in the needle component passageway;

the blunting component and the needle component being movable relative to each other from an insertion configuration, in which the puncture tip of the needle cannula extends beyond the blunt end of the blunting member, to a blunted configuration, in which the blunt distal end of the blunting member protrudes beyond the puncture tip of the needle cannula, thus blunting the needle cannula; and a drive member rotatably engaging the needle component and the blunting component for moving the apparatus from the insertion configuration to the blunted configuration.

15. The apparatus of claim 14 wherein the drive member comprises a screw thread engagement between the blunting component and the needle component.

16. A needle apparatus having a fluid flow passageway and a proximal aperture for fluid flow therethrough, the apparatus comprising:

a needle component having a needle component passageway therethrough and comprising a hub portion and a needle cannula, the needle cannula having a longitudinal axis and being joined to, and extending from, the hub portion and having a proximal end and a puncture tip;

a blunting component comprising a blunting member and a blunting member hub, the blunting member having a proximal end and a blunt distal end, the blunting member being joined to, and extending from, the blunting member hub and being dimensioned and configured to be received in the needle component passageway;

the blunting component and the needle component being movable relative to each other from an insertion configuration, in which the puncture tip of the needle cannula extends beyond the blunt end of the blunting member, to a blunted configuration, in which the blunt distal end of the blunting member protrudes beyond the puncture tip of the needle cannula, thus blunting the needle cannula; and wherein the needle component comprises a compressible pliant portion and wherein the blunting member hub is disposed within the pliant portion and is dimensioned and configured to move from the insertion configuration to the blunted configuration upon compression of the pliant portion of the needle component.

17. The apparatus of claim 16 comprising a fluid flow passageway therethrough, wherein the pliant portion comprises a working fluid reservoir configured to isolate a working fluid therein from the fluid flow passageway, and wherein the oblique motion deployment means comprises a piston and cylinder engagement of the blunting component and the needle component.

18. The apparatus of claim 14 wherein the blunting member hub comprises a shuttle portion and wherein the drive member comprises a cam surface that bears upon the shuttle portion, the apparatus being configured to permit the shuttle portion to serve as a cam follower to move the apparatus from the insertion configuration to the blunting configuration in response to rotation of the drive member relative to the needle component.

19. The apparatus of claim 2 or claim 3 having a proximal aperture for flow of biologic fluids through the apparatus, wherein the blunting component and the needle component are disposed in a tandem configuration wherein the blunting component defines the proximal aperture of the apparatus.

20. The apparatus of claim 2 or claim 4 having a proximal aperture for flow of biologic fluids through the apparatus, wherein the needle component defines the proximal aperture of the apparatus.

21. The apparatus of claim 2 or claim 3 having a proximal aperture for flow of biologic fluids through the apparatus, wherein the drive member is disposed in tandem relation to the needle component and defines the proximal aperture of the apparatus.

22. The apparatus of any one of claim 2, claim 4 or claim 13 comprising locking means for locking the apparatus in the blunted configuration.

23. The apparatus of claim 22 wherein the locking means comprises a spline and cam channel engagement between the blunting component and the needle component.

24. The apparatus of claim 22 wherein the locking means comprises (i) a detent on one of the needle component and the blunting component, and (ii) a ramp on the other, the ramp defining a shoulder, and wherein the detent is positioned and configured to ride up the ramp as the blunting member is advanced to be positioned to bear against the shoulder to inhibit rearward movement after the blunted configuration is attained.

25. The apparatus of claim 24 further comprising a return ramp for permitting the detent to move axially past the shoulder so that the apparatus can return to the insertion configuration.

26. The apparatus of claim 22 wherein the locking means comprises a detent and an axially-extending slot arrangement wherein the detent is positioned and configured to move axially in the slot as the blunting member is advanced, and wherein the slot is configured to define a pinch region through which the detent passes, the pinch region being configured to inhibit entry of the detent into the slot once the blunted configuration is attained.

27. The apparatus of claim 24 further comprising a return ramp for permitting the detent to move axially past the shoulder so that the apparatus can return to the insertion configuration.

28. A needle apparatus having a fluid flow passageway therethrough, the apparatus comprising:
a cannula component comprising a needle cannula on a needle hub and a blunting member on a blunting member hub, the needle cannula having a longitudinal axis, a puncture tip, having a needle passageway therethrough and the blunting member having a blunt end, the needle cannula and the blunting member being disposed telescopically one within the other and being configured for movement from an insertion configuration, in which the puncture tip of the needle cannula extends beyond the blunt end of the blunting member, to a blunted configuration, in which the blunt end of the blunting member extends beyond the puncture tip, to blunt the needle cannula; and
a drive member rotatably engaging the needle hub and the blunting hub for moving the apparatus from the insertion configuration to the blunted configuration.

29. A needle apparatus having a fluid flow passageway and a proximal aperture for fluid flow therethrough, the apparatus comprising:
a needle component having a needle component passageway therethrough and comprising a hub portion and a needle cannula, the needle cannula having a longitudinal axis and being joined to, and extending from, the hub portion and having a proximal end and a puncture tip;
a blunting component comprising a blunting member and a blunting member hub, the blunting member having a proximal end and a blunt distal end, the blunting member being joined to, and extending from, the blunting member hub and being dimensioned and configured to be received in the needle component passageway;
the blunting component and the needle component being movable relative to each other from an insertion configuration, in which the puncture tip of the needle cannula extends beyond the blunt end of the blunting member, to a blunted configuration, in which the blunt distal end of the blunting member protrudes beyond the puncture tip of the needle cannula, thus blunting the needle cannula; and
means comprising a diverted tension line for moving the apparatus from the insertion configuration to the blunted configuration.

30. A needle apparatus having a fluid flow passage therethrough, the apparatus comprising:
a needle component having a needle component passageway therethrough and comprising a hub portion and a needle cannula, the needle cannula having a longitudinal axis and being joined to, and extending from, the hub portion and having a proximal end and a puncture tip;
a blunting component comprising a blunting member and a blunting member hub, the blunting member having a proximal end and a blunt distal end and being joined to, and extending from, the blunting member hub and being dimensioned and configured to be received in the needle component passageway;
the blunting component and the needle component being movable relative to each other from an insertion configuration, in which the puncture tip of the needle cannula extends beyond the blunt end of the blunting member, to a blunted configuration, in which the blunt distal end of the blunting member protrudes beyond the puncture tip of the needle cannula, thus blunting the needle cannula; and
a drive member that rotatably engages the needle component, for moving the apparatus from the insertion configuration to the blunted configuration;
wherein the drive member is rotatable about an axis that is disposed transversely to the longitudinal axis of the needle cannula.

31. A needle apparatus comprising:
a needle component having a needle component passageway therethrough and comprising a hub portion and a needle cannula, the needle cannula having a longitudinal axis and being joined to, and extending from, the hub portion and having a proximal end and a puncture tip;
a blunting component comprising a blunting member and a blunting member hub, the blunting member having a proximal end and a blunt distal end, the blunting member being joined to, and extending from, the blunting member hub and being dimensioned and configured to be received in the needle component passageway;

the blunting component and the needle component being movable relative to each other from an insertion configuration, -in-which-the puncture tip of the needle cannula extends beyond the blunt end of the blunting member, to a blunted configuration, in which the blunt distal end of the blunting member protrudes beyond the puncture tip of the needle cannula, thus blunting the needle cannula; and a contrary motion mechanism for moving the blunting member forward relative to the needle cannula in response to a rearward motion imposed by the user, the contrary motion mechanism comprising a lever.

32. A needle apparatus comprising:

a needle component comprising a hub portion and a needle cannula, the needle cannula having a longitudinal axis and being joined to, and extending from, the hub portion and having a proximal end at the hub portion and having a distal end comprising a puncture tip, the hub portion and the needle cannula cooperating to define a needle component passageway;

a blunting component comprising a blunting member having a blunt proximal end and a distal end, the blunting component being dimensioned and configured to be received in the needle component passageway;

the blunting component and the needle component being non-hydraulically movable relative to each other from an insertion configuration, in which the puncture tip of the needle cannula extends beyond the blunt end of the blunting member, to a blunted configuration, in which the blunt proximal end of the blunting member protrudes beyond the puncture tip of the needle cannula, thus blunting the needle cannula;

a pair of wings that are connected to the needle component, the wings being displaceable about a displacement axis that is aligned with the longitudinal axis of the needle cannula and being movable between a manipulation position and a neutral position; and a tension line secured to the wings and being connected to the blunting component, the tension line being configured so movement of the wings from the manipulation position to the neutral position causes the tension line to move the apparatus from the insertion configuration to the blunted configuration.

33. A needle apparatus comprising:

a hollow body, the body having a distal end and a proximal end and defining a cavity extending along a body axis from the distal end to the proximal end of the body;

the cavity including a first generally conical region disposed at the distal end of the body, a first generally cylindrical region coaxially disposed adjacent the first conical region, a second generally cylindrical region coaxially disposed adjacent the first cylindrical region, a second generally conical region coaxially disposed adjacent the second cylindrical region and a third generally cylindrical region coaxially disposed adjacent the second conical region and extending therefrom to the proximal end of the body, the diameter of the second cylindrical region being less than that of the first cylindrical region and the diameter of the third cylindrical region being greater than that of the second cylindrical region;

a cannula having a forward end and a terminal end, the outer diameter of the cannula being substantially equal to the diameter of the first cylindrical region of the cavity, the terminal end of the cannula being received within the first cylindrical region such that the forward end extends forwardly of the distal end of the body and the cannula extends along the body axis;

a movable member at least partially disposed within the body cavity and having a forward end and an outer diameter which is not greater than either of the inner diameter of the cannula or the diameter of the second cylindrical region of the cavity, the movable member extending through the second cylindrical region of the cavity and being at least partially movably received within the cannula;

one of the forward end of the cannula the forward end of the movable member having a tissue puncture tip and the other of the forward end of the cannula or the forward end of the movable member having a blunt tip.

34. A needle apparatus comprising:

a needle component having a needle component passageway therethrough and comprising a hub portion and a needle cannula, the needle cannula having a longitudinal axis and being joined to, and extending from, the hub portion and having a proximal end and a puncture tip;

a blunting component comprising a blunting member having a proximal end and a blunt distal end, the blunting component being dimensioned and configured to be received in the needle component passageway;

the blunting component and the needle component being movable relative to each other from an insertion configuration, in which the puncture tip of the needle cannula extends beyond the blunt end of the blunting member, to a blunted configuration, in which the blunt distal end of the blunting member protrudes beyond the puncture tip of the needle cannula, thus blunting the needle cannula;

an oblique motion deployment means for moving the apparatus from the insertion configuration to the blunted configuration;

a haft connected to the needle component for use in manipulation of the needle cannula without moving the apparatus from the insertion configuration to the blunted configuration, locking means for locking the apparatus in the blunted configuration wherein the locking means comprises (i) a detent on one of the needle component and the blunting component, and (ii) a ramp on the other, the ramp defining a shoulder, and wherein the detent is positioned and configured to ride up the ramp as the blunting member is advanced to be positioned to bear against the shoulder to inhibit rearward movement after the blunted configuration is attained, and a return ramp for permitting the detent to move axially past the shoulder so that the apparatus can return to the sharpened configuration.

* * * * *